US011753450B2

(12) United States Patent
Zong

(10) Patent No.: US 11,753,450 B2
(45) Date of Patent: Sep. 12, 2023

(54) ALKALI-TOLERANT AFFINITY CHROMATOGRAPHY LIGANDS

(71) Applicant: Bioprocessia Technologies LLC, San Diego, CA (US)

(72) Inventor: Yinong Zong, San Diego, CA (US)

(73) Assignee: Bioprocessia Technologies LLC, San Diego, CA (US)

( * ) Notice: Subject to any disclaimer, the term of this patent is extended or adjusted under 35 U.S.C. 154(b) by 30 days.

(21) Appl. No.: 16/919,827

(22) Filed: Jul. 2, 2020

(65) Prior Publication Data

US 2021/0032296 A1 Feb. 4, 2021

Related U.S. Application Data

(60) Provisional application No. 62/966,743, filed on Jan. 28, 2020, provisional application No. 62/870,314, filed on Jul. 3, 2019.

(51) Int. Cl.
C07K 14/31 (2006.01)
B01D 15/38 (2006.01)

(52) U.S. Cl.
CPC .......... C07K 14/31 (2013.01); B01D 15/3809 (2013.01)

(58) Field of Classification Search
CPC ....... B01D 15/3809; C07K 14/31; C07K 1/22
See application file for complete search history.

(56) References Cited

U.S. PATENT DOCUMENTS

| 7,709,209 | B2 | 5/2010 | Hober et al. |
| 7,834,158 | B2 | 11/2010 | Hober |
| 8,198,404 | B2 | 6/2012 | Hober |
| 8,329,860 | B2 | 12/2012 | Hall et al. |
| 8,354,510 | B2 | 1/2013 | Hober et al. |
| 8,772,447 | B2 | 7/2014 | Hall et al. |
| 9,051,375 | B2 | 6/2015 | Li et al. |
| 9,156,892 | B2 | 10/2015 | Hober |
| 9,290,549 | B2 | 3/2016 | Hall et al. |
| 9,296,791 | B2 | 3/2016 | Hober et al. |
| 9,403,883 | B2 | 8/2016 | Yoshida et al. |
| 9,534,023 | B2 | 1/2017 | Hober |
| 9,663,559 | B2 | 5/2017 | Hall et al. |
| 10,213,765 | B2 | 2/2019 | Hall et al. |
| 10,343,142 | B2 | 7/2019 | Hall et al. |
| 10,808,042 | B2 | 10/2020 | Haupts |
| 2005/0143566 | A1* | 6/2005 | Hober .................... B01J 20/289 530/388.4 |
| 2006/0194950 | A1 | 8/2006 | Hober et al. |
| 2017/0080358 | A1 | 3/2017 | Hober |
| 2019/0308168 | A1 | 10/2019 | Hall et al. |

FOREIGN PATENT DOCUMENTS

| CN | 1642976 | 7/2005 |
| CN | 101522278 | 9/2009 |
| CN | 102365361 | 2/2012 |
| CN | 102532284 | 7/2012 |
| CN | 103403020 | 11/2013 |
| CN | 106422418 | 2/2017 |
| CN | 107922483 | 4/2018 |
| EP | 2412809 | 2/2012 |
| WO | WO 2003/080655 | 10/2003 |
| WO | WO 2008/039141 | 4/2008 |
| WO | WO 2010/110288 | 9/2010 |
| WO | WO 2012/083425 | 6/2012 |
| WO | WO 2017/009421 | 1/2017 |

OTHER PUBLICATIONS

Sara Kanje, Protein Engineering Allows for Mild Affinity-based Elution of Therapeutic Antibodies, J Mol Biol (2018) 430, 3427-3438.*
Kalinowska et al., "Is the hydrophobic core a universal structural element in proteins?," Journal of Molecular Modeling, Jul. 2017, 23(7):1-6.
Kimple et al., "Overview of affinity tags for protein purification," Current Protocols in Protein Science, May 2004, 36(1):9.
Levinthal, "How to fold graciously," Mossbauer Spectroscopy in Biological Systems: Proceedings of a meeting held at Allerton House, Monticello, Illinois, Mar. 17, 1969, 67:22-4.
Magdeldin et al. "Affinity chromatography: Principles and applications," Magdeldin (eds.), Mar. 21, 2012, 26 pages.
Minakuchi et al., "Remarkable alkaline stability of an engineered protein A as immunoglobulin affinity ligand: C domain having only one amino acid substitution," Protein Science, Sep. 2013, 22(9):1230-8.
Nilsson et al., "A synthetic IgG-binding domain based on staphylococcal protein A," Protein Engineering, Design and Selection, Feb. 1, 1987, 1(2):107-13.

* cited by examiner

Primary Examiner — Julie Ha
Assistant Examiner — Erinne R Dabkowski
(74) Attorney, Agent, or Firm — Fish & Richardson P.C.

(57) ABSTRACT

The Sequence Listing associated with this application is provided in text form in lieu of a paper copy, and is hereby incorporated by reference into the specification. The name of the text file containing the Sequence Listing is Sequence-Listing.txt. The text file is 36.3 KB, and was created on Sep. 30, 2020.

19 Claims, 12 Drawing Sheets
Specification includes a Sequence Listing.

```
• E: -ADAQQNNFNKDQQSAFYEILNMPNLNEAQRNGFIQSLKDDPSQ TNVLGEAKKL ESQAPK 61
• D: AAN---AAQHDEAQQNAFYQVLNMPNLNADQRNGFIQSLKDDPSQ ANVLGEAQKL DSQAPK 60
• A: -AD----NNFNKEQQNAFYEILNMPNLNEEQRNGFIQSLKDDPSQ ANLLSEAKKL ESQAPK 58
• B: -AD----NKFNKEQQNAFYEILHLPNLNEEQRNGFIQSLKDDPSQ ANLLAEAKKL DAQAPK 58
• C: -AD----NKFNKEQQNAFYEILHLPNLTEEQRNGFIQSLKDDPSV KEILAEAKKL DAQAPK 58
• Z: -VD----NKFNKEQQNAFYEILHLPNLNEEQRNAFIQSLKDDPSQ ANLLAEAKKL DAQAPK 58
```

FIG. 1

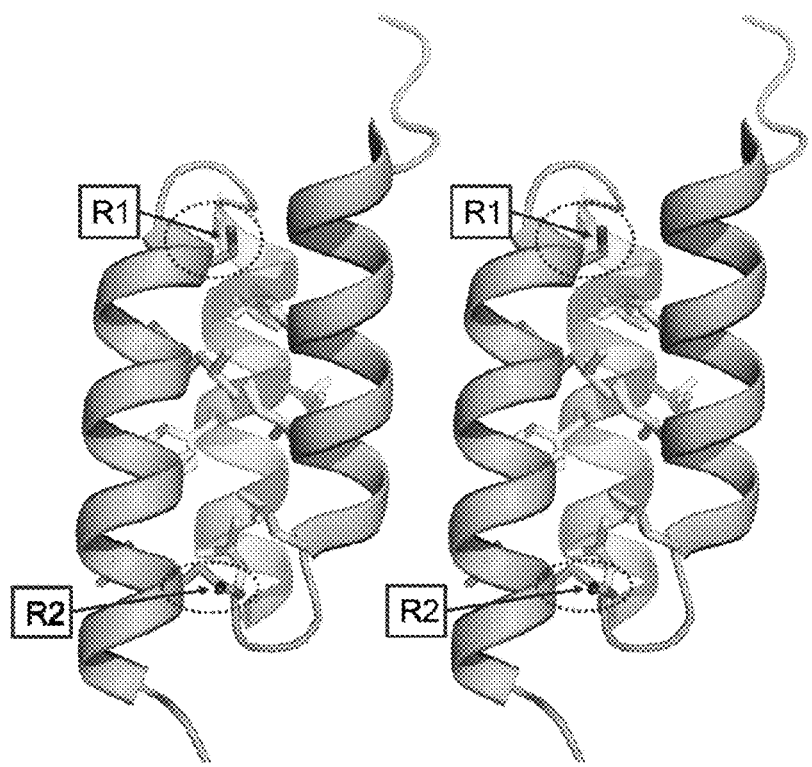

FIG. 2

| | | |
|---|---|---|
| N | VDNKFNKEQQNAFYEILHLPNLNEEQRNAFIQSLKDDPSQSANLLAEAKKLNDAQAPK | 58 |
| C | ADNKFNKEQQNAFYEILHLPNLTEEQRNGFIQSLKDDPSVSKEILAEAKKLNDAQAPK | 58 |
| 9B | VDNKFNKEQQNAFYEILHLPNLTEEQRNKFIQSLKDDPSQAKEILAEAKKLNDAQAPK | 58 |
| 9F | VDNKFNKEQQNAFYEILHLPNLTEEQRNKFIQSLKDDPSQLKEILAEAKKLNDAQAPK | 58 |
| 8E | VDNKFNKEQQNAFYEILHLPNLTEEQRQKFIQSLKDDPSQAKEILAEAKKLVDAQAPK | 58 |
| 8C | VDNKFNKEQQNAFYEILHLPNLTEEQRNKFIQSLKDDPSQSKEILAEAKKLNDAQAPK | 58 |
| | *:****************.:.***********..*:****:**** | |

SEQ ID NO. 1: E domain
ORGANISM: Staphylococcus aureus

ADAQQNNFNKDQQSAFYEILNMPNLNEAQRNGFIQSLKDDPSQSTNVLGEAKKLNESQAPK

SEQ ID NO. 2: D domain
ORGANISM: Staphylococcus aureus

AANAAQHDEAQQNAFYQVLNMPNLNADQRNGFIQSLKDDPSQSANVLGEAQKLNDSQAPK

SEQ ID NO. 3: A domain
ORGANISM: Staphylococcus aureus

ADNNFNKEQQNAFYEILNMPNLNEEQRNGFIQSLKDDPSQSANLLSEAKKLNESQAPK

SEQ ID NO. 4: B domain
ORGANISM: Staphylococcus aureus

ADNKFNKEQQNAFYEILHLPNLNEEQRNGFIQSLKDDPSQSANLLAEAKKLNDAQAPK

SEQ ID NO. 5: C domain
ORGANISM: Staphylococcus aureus

ADNKFNKEQQNAFYEILHLPNLTEEQRNGFIQSLKDDPSVSKEILAEAKKLNDAQAPK

SEQ ID NO. 6: Z domain
ORGANISM: Artificial Sequence

VDNKFNKEQQNAFYEILHLPNLNEEQRNAFIQSLKDDPSQSANLLAEAKKLNDAQAPK

SEQ ID NO. 7:
ORGANISM: Artificial Sequence
VDNKFNKEQQNAFYEILHLPNLNEEQRNAFIQSLKDDPSQAANLLAEAKKLNDAQAPK

SEQ ID NO. 8:
ORGANISM: Artificial Sequence
VDNKFNKEQQNAFYEILHLPNLNEEQRNAFIQSLKDDPSQVANLLAEAKKLNDAQAPK

SEQ ID NO. 9:
ORGANISM: Artificial Sequence
VDNKFNKEQQNAFYEILHLPNLNEEQRNAFIQSLKDDPSQSANLLAEAKKLLDAQAPK

SEQ ID NO. 10:

FIG. 9 (Continued)

ORGANISM: Artificial Sequence
VDNKFNKEQQNAFYEILHLPNLNEEQRNAFIQSLKDDPSQSANLLAEAKKLVDAQAPK

SEQ ID NO. 11:
ORGANISM: Artificial Sequence
VDNKFNKEQQNAFYEILHLPNLNEEQRNAFIQSLKDDPSQAANLLAEAKKLVDAQAPK

SEQ ID NO. 12:
ORGANISM: Artificial Sequence
VDNKFNKEQQNAFYEILHLPNLNEEQRNAFIQSLKDDPSQVANLLAEAKKLVDAQAPK

SEQ ID NO. 13:
ORGANISM: Artificial Sequence
VDNKFNKEQQNAFYEILHLPNLNEEQRNAFIQSLKDDPSQAANLLAEAKKLLDAQAPK

SEQ ID NO. 14:
ORGANISM: Artificial Sequence

MVDNKFNKEQQNAFYEILHLPNLNEEQRNAFIQSLKDDPSQSANLLAEAKKLNDAQAPK
VDNKFNKEQQNAFYEILHLPNLNEEQRNAFIQSLKDDPSQSANLLAEAKKLNDAQAPK
VDNKFNKEQQNAFYEILHLPNLNEEQRNAFIQSLKDDPSQSANLLAEAKKLNDAQAPK
VDNKFNKEQQNAFYEILHLPNLNEEQRNAFIQSLKDDPSQSANLLAEAKKLNDAQAPK
VDNKFNKEQQNAFYEILHLPNLNEEQRNAFIQSLKDDPSQSANLLAEAKKLNDAQAPK
HHHHHHCKCC

SEQ ID NO. 15:
ORGANISM: Artificial Sequence

MADNKFNKEQQNAFYEILHLPNLTEEQRNAFIQSLKDDPSVSKEILAEAKKLNDAQAPK
ADNKFNKEQQNAFYEILHLPNLTEEQRNAFIQSLKDDPSVSKEILAEAKKLNDAQAPK
ADNKFNKEQQNAFYEILHLPNLTEEQRNAFIQSLKDDPSVSKEILAEAKKLNDAQAPK
ADNKFNKEQQNAFYEILHLPNLTEEQRNAFIQSLKDDPSVSKEILAEAKKLNDAQAPK
ADNKFNKEQQNAFYEILHLPNLTEEQRNAFIQSLKDDPSVSKEILAEAKKLNDAQAPK
HHHHHHCKCC

SEQ ID NO. 16:
ORGANISM: Artificial Sequence

MVDNKFNKEQQNAFYEILHLPNLNEEQRNAFIQSLKDDPSQAANLLAEAKKLNDAQAPK
VDNKFNKEQQNAFYEILHLPNLNEEQRNAFIQSLKDDPSQAANLLAEAKKLNDAQAPK
VDNKFNKEQQNAFYEILHLPNLNEEQRNAFIQSLKDDPSQAANLLAEAKKLNDAQAPK
VDNKFNKEQQNAFYEILHLPNLNEEQRNAFIQSLKDDPSQAANLLAEAKKLNDAQAPK
VDNKFNKEQQNAFYEILHLPNLNEEQRNAFIQSLKDDPSQAANLLAEAKKLNDAQAPK
HHHHHHCKCC

SEQ ID NO. 17:
ORGANISM: Artificial Sequence

FIG. 9 (Continued)

```
MVDNKFNKEQQNAFYEILHLPNLNEEQRNAFIQSLKDDPSQVANLLAEAKKLNDAQAPK
VDNKFNKEQQNAFYEILHLPNLNEEQRNAFIQSLKDDPSQAVNLLAEAKKLNDAQAPK
VDNKFNKEQQNAFYEILHLPNLNEEQRNAFIQSLKDDPSQAVNLLAEAKKLNDAQAPK
VDNKFNKEQQNAFYEILHLPNLNEEQRNAFIQSLKDDPSQAVNLLAEAKKLNDAQAPK
VDNKFNKEQQNAFYEILHLPNLNEEQRNAFIQSLKDDPSQAVNLLAEAKKLNDAQAPK
HHHHHHCKCC
```

SEQ ID NO. 18:
ORGANISM: Artificial Sequence

```
MVDNKFNKEQQNAFYEILHLPNLNEEQRNAFIQSLKDDPSQSANLLAEAKKLLDAQAPK
VDNKFNKEQQNAFYEILHLPNLNEEQRNAFIQSLKDDPSQSANLLAEAKKLLDAQAPK
VDNKFNKEQQNAFYEILHLPNLNEEQRNAFIQSLKDDPSQSANLLAEAKKLLDAQAPK
VDNKFNKEQQNAFYEILHLPNLNEEQRNAFIQSLKDDPSQSANLLAEAKKLLDAQAPK
VDNKFNKEQQNAFYEILHLPNLNEEQRNAFIQSLKDDPSQSANLLAEAKKLLDAQAPK
HHHHHHCKCC
```

SEQ ID NO. 19:
ORGANISM: Artificial Sequence

```
MVDNKFNKEQQNAFYEILHLPNLNEEQRNAFIQSLKDDPSQSANLLAEAKKLVDAQAPK
VDNKFNKEQQNAFYEILHLPNLNEEQRNAFIQSLKDDPSQSANLLAEAKKLVDAQAPK
VDNKFNKEQQNAFYEILHLPNLNEEQRNAFIQSLKDDPSQSANLLAEAKKLVDAQAPK
VDNKFNKEQQNAFYEILHLPNLNEEQRNAFIQSLKDDPSQSANLLAEAKKLVDAQAPK
VDNKFNKEQQNAFYEILHLPNLNEEQRNAFIQSLKDDPSQSANLLAEAKKLVDAQAPK
HHHHHHCKCC
```

SEQ ID NO. 20:
ORGANISM: Artificial Sequence

```
MVDNKFNKEQQNAFYEILHLPNLNEEQRNAFIQSLKDDPSQAANLLAEAKKLVDAQAPK
VDNKFNKEQQNAFYEILHLPNLNEEQRNAFIQSLKDDPSQAANLLAEAKKLVDAQAPK
VDNKFNKEQQNAFYEILHLPNLNEEQRNAFIQSLKDDPSQAANLLAEAKKLVDAQAPK
VDNKFNKEQQNAFYEILHLPNLNEEQRNAFIQSLKDDPSQAANLLAEAKKLVDAQAPK
VDNKFNKEQQNAFYEILHLPNLNEEQRNAFIQSLKDDPSQAANLLAEAKKLVDAQAPK
HHHHHHCKCC
```

SEQ ID NO. 21:
ORGANISM: Artificial Sequence

```
MVDNKFNKEQQNAFYEILHLPNLNEEQRNAFIQSLKDDPSQVANLLAEAKKLVDAQAPK
VDNKFNKEQQNAFYEILHLPNLNEEQRNAFIQSLKDDPSQVANLLAEAKKLVDAQAPK
VDNKFNKEQQNAFYEILHLPNLNEEQRNAFIQSLKDDPSQVANLLAEAKKLVDAQAPK
VDNKFNKEQQNAFYEILHLPNLNEEQRNAFIQSLKDDPSQVANLLAEAKKLVDAQAPK
VDNKFNKEQQNAFYEILHLPNLNEEQRNAFIQSLKDDPSQVANLLAEAKKLVDAQAPK
HHHHHHCKCC
```

SEQ ID NO. 22:
ORGANISM: Artificial Sequence

FIG. 9 (Continued)

```
MVDNKFNKEQQNAFYEILHLPNLNEEQRNAFIQSLKDDPSQAANLLAEAKKLLDAQAPK
VDNKFNKEQQNAFYEILHLPNLNEEQRNAFIQSLKDDPSQAANLLAEAKKLLDAQAPK
VDNKFNKEQQNAFYEILHLPNLNEEQRNAFIQSLKDDPSQAANLLAEAKKLLDAQAPK
VDNKFNKEQQNAFYEILHLPNLNEEQRNAFIQSLKDDPSQAANLLAEAKKLLDAQAPK
VDNKFNKEQQNAFYEILHLPNLNEEQRNAFIQSLKDDPSQAANLLAEAKKLLDAQAPK
HHHHHHCKCC
```

SEQ ID NO: 23
LIENGTH: 18
ORGANISM: Bacillus stearothermophilus
OTHER INFORMATION: Connecting Helix of ribosomal protein L9

Glu Ala Gln Lys Gln Lys Glu Gln Arg Gln Ala Ala Glu Glu Leu
1               5                   10                  15

Ala Asn Ala

SEQ ID NO: 24
LENGTH: 20
ORGANISM: Homo Sapiens
OTHER INFORMATION: Glucagon

Thr Ser Asp Tyr Ser Lys Tyr Leu Asp Ser Arg Arg Ala Gln Asp Phe Val
Gln Trp Leu

SEQ ID NO: 25
LENGTH: 23
ORGANISM: Paramecium tetraurelia
OTHER INFORMATION: Calmodulin Phe Leu Ser Leu Met Ala Arg Lys Met Lys Glu Gln Asp Ser Glu Glu Glu
Leu Ile Glu Ala Phe Lys

SEQ ID NO: 26
LENGTH: 27
ORGANISM: Homo Sapiens
OTHER INFORMATION: Myosin-10

Glu Ile Asp Ser Thr Trp Ser Ala Leu Glu Lys Ala Glu Gln Glu His Ala
Glu Ala Leu Arg Ile Glu Leu Lys Arg Gln

SEQ ID NO: 27
LENGTH: 75
ORGANISM: Homo Sapiens
OTHER INFORMATION: Sumo1

FIG. 9 (Continued)

```
Glu Gly Glu Tyr Ile Lys Leu Lys Val Ile Gly Gln Asp Ser Ser Glu Ile
His Phe Lys Val Lys Met Thr Thr His Leu Lys Lys Leu Lys Glu Ser Tyr
Cys Gln Arg Gln Gly Val Pro Met Asn Ser Leu Arg Phe Leu Phe Glu Gly
Gln Arg Ile Ala Asp Asn His Thr Pro Lys Glu Leu Gly Met Glu Glu Glu
Asp Val Ile Glu Val Tyr Gln
```

SEQ ID NO: 28
LENGTH: 48
ORGANISM: Homo Sapiens
OTHER INFORMATION: EGF-Like Domain of heregulin-alpha

```
Asn Ser Tyr Pro Gly Cys Pro Ser Ser Tyr Asp Gly Tyr Cys Leu Asn Gly
Gly Val Cys Met His Ile Glu Ser Leu Asp Ser Tyr Thr Cys Asn Cys Val
Ile Gly Tyr Ser Gly Asp Arg Cys Gln Thr Arg Asp Leu Arg
```

SEQ ID NO: 29
LENGTH: 40
ORGANISM: Homo Sapiens
OTHER INFORMATION: UBA domain of Rad23A

```
Ser Glu Tyr Glu Thr Met Leu Thr Glu Ile Met Ser Met Gly Tyr Glu Arg
Glu Arg Val Val Ala Ala Leu Arg Ala Ser Tyr Asn Asn Pro His Arg Ala
Val Glu Tyr Leu Leu Thr
```

SEQ ID NO: 30 (9B domain)
TYPE: PRT
ORGANISM: Artificial Sequence

VDNKFNKEQQNAFYEILHLPNLTEEQRNKFIQSLKDDPSQAKEILAEAKKLNDAQAPK

SEQ ID NO: 31 (9F domain)
TYPE: PRT
ORGANISM: Artificial Sequence

VDNKFNKEQQNAFYEILHLPNLTEEQRNKFIQSLKDDPSQLKEILAEAKKLNDAQAPK

SEQ ID NO: 32 (8E domain)
TYPE: PRT
ORGANISM: Artificial Sequence

VDNKFNKEQQNAFYEILHLPNLTEEQRQKFIQSLKDDPSQAKEILAEAKKLVDAQAPK

SEQ ID NO: 33 (8C domain)
TYPE: PRT
ORGANISM: Artificial Sequence

VDNKFNKEQQNAFYEILHLPNLTEEQRNKFIQSLKDDPSQSKEILAEAKKLNDAQAPK

SEQUENCE LISTING

```
<160> NUMBER OF SEQ ID NOS: 33

<210> SEQ ID NO 1
<211> LENGTH: 61
<212> TYPE: PRT
<213> ORGANISM: Staphylococcus aureus

<400> SEQUENCE: 1

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45
```

```
Gly Glu Ala Lys Lys Leu Asn Glu Ser Gln Ala Pro Lys
    50                  55                  60

<210> SEQ ID NO 2
<211> LENGTH: 60
<212> TYPE: PRT
<213> ORGANISM: Staphylococcus aureus

<400> SEQUENCE: 2

Ala Ala Asn Ala Ala Gln His Asp Glu Ala Gln Gln Asn Ala Phe Tyr
1               5                   10                  15

Gln Val Leu Asn Met Pro Asn Leu Asn Ala Asp Gln Arg Asn Gly Phe
            20                  25                  30

Ile Gln Ser Leu Lys Asp Asp Pro Ser Gln Ser Ala Asn Val Leu Gly
        35                  40                  45

Glu Ala Gln Lys Leu Asn Asp Ser Gln Ala Pro Lys
    50                  55                  60

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45
```

```
Lys Lys Leu Asn Asp Ala Gln Ala Pro Lys
    50                  55
```

```
<210> SEQ ID NO 6
<211> LENGTH: 58
<212> TYPE: PRT
<213> ORGANISM: Artificial Sequence
<220> FEATURE:
<223> OTHER INFORMATION: Z domain

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: S41A (Z domain)

<400> SEQUENCE: 7

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ala Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: S41V (Z domain)

<400> SEQUENCE: 8

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Val Ala Asn Leu Leu Ala Glu Ala
        35                  40                  45

Lys Lys Leu Asn Asp Ala Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: N52L (Z domain)

<400> SEQUENCE: 9
```

```
Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Leu Asp Ala Gln Ala Pro Lys
        50                  55

<210> SEQ ID NO 10
<211> LENGTH: 58
<212> TYPE: PRT
<213> ORGANISM: Artificial Sequence
<220> FEATURE:
<223> OTHER INFORMATION: N52V (Z domain)

<400> SEQUENCE: 10

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Val Asp Ala Gln Ala Pro Lys
        50                  55

<210> SEQ ID NO 11
<211> LENGTH: 58
<212> TYPE: PRT
<213> ORGANISM: Artificial Sequence
<220> FEATURE:
<223> OTHER INFORMATION: S41A, N52V (Z domain)

<400> SEQUENCE: 11

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ala Ala Asn Leu Leu Ala Glu Ala
        35                  40                  45

Lys Lys Leu Val Asp Ala Gln Ala Pro Lys
        50                  55

<210> SEQ ID NO 12
<211> LENGTH: 58
<212> TYPE: PRT
<213> ORGANISM: Artificial Sequence
<220> FEATURE:
<223> OTHER INFORMATION: S41V, N52V (Z domain)

<400> SEQUENCE: 12

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Val Ala Asn Leu Leu Ala Glu Ala
        35                  40                  45

Lys Lys Leu Val Asp Ala Gln Ala Pro Lys
        50                  55
```

```
<210> SEQ ID NO 13
<211> LENGTH: 58
<212> TYPE: PRT
<213> ORGANISM: Artificial Sequence
<220> FEATURE:
<223> OTHER INFORMATION: S41A, V52L (Z domain)

<400> SEQUENCE: 13

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ala Ala Asn Leu Leu Ala Glu Ala
        35                  40                  45

Lys Lys Leu Leu Asp Ala Gln Ala Pro Lys
    50                  55

<210> SEQ ID NO 14
<211> LENGTH: 301
<212> TYPE: PRT
<213> ORGANISM: Artificial Sequence
<220> FEATURE:
<223> OTHER INFORMATION: Z domain (without mutations)

<400> SEQUENCE: 14

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys Val Asp Asn Lys Phe
    50                  55                  60

Asn Lys Glu Gln Gln Asn Ala Phe Tyr Glu Ile Leu His Leu Pro Asn
65                  70                  75                  80

Leu Asn Glu Glu Gln Arg Asn Ala Phe Ile Gln Ser Leu Lys Asp Asp
                85                  90                  95

Pro Ser Gln Ser Ala Asn Leu Leu Ala Glu Ala Lys Lys Leu Asn Asp
            100                 105                 110

Ala Gln Ala Pro Lys Val Asp Asn Lys Phe Asn Lys Glu Gln Gln Asn
        115                 120                 125

Ala Phe Tyr Glu Ile Leu His Leu Pro Asn Leu Asn Glu Glu Gln Arg
    130                 135                 140

Asn Ala Phe Ile Gln Ser Leu Lys Asp Asp Pro Ser Gln Ser Ala Asn
145                 150                 155                 160

Leu Leu Ala Glu Ala Lys Lys Leu Asn Asp Ala Gln Ala Pro Lys Val
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Ala Phe Ile Gln Ser
        195                 200                 205

Leu Lys Asp Asp Pro Ser Gln Ser Ala Asn Leu Leu Ala Glu Ala Lys
    210                 215                 220

Lys Leu Asn Asp Ala Gln Ala Pro Lys Val Asp Asn Lys Phe Asn Lys
225                 230                 235                 240

Glu Gln Gln Asn Ala Phe Tyr Glu Ile Leu His Leu Pro Asn Leu Asn
                245                 250                 255
```

```
Glu Glu Gln Arg Asn Ala Phe Ile Gln Ser Leu Lys Asp Asp Pro Ser
                260                 265                 270

Gln Ser Ala Asn Leu Leu Ala Glu Ala Lys Lys Leu Asn Asp Ala Gln
            275                 280                 285

Ala Pro Lys His His His His His Cys Lys Cys Cys
        290                 295                 300

<210> SEQ ID NO 15
<211> LENGTH: 301
<212> TYPE: PRT
<213> ORGANISM: Artificial Sequence
<220> FEATURE:
<223> OTHER INFORMATION: G29A (C domain with G29A mutation)

<400> SEQUENCE: 15

Met Ala Asp Asn Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys Ala Asp Asn Lys Phe
    50                  55                  60

Asn Lys Glu Gln Gln Asn Ala Phe Tyr Glu Ile Leu His Leu Pro Asn
65                  70                  75                  80

Leu Thr Glu Glu Gln Arg Asn Ala Phe Ile Gln Ser Leu Lys Asp Asp
                85                  90                  95

Pro Ser Val Ser Lys Glu Ile Leu Ala Glu Ala Lys Lys Leu Asn Asp
            100                 105                 110

Ala Gln Ala Pro Lys Ala Asp Asn Lys Phe Asn Lys Glu Gln Gln Asn
        115                 120                 125

Ala Phe Tyr Glu Ile Leu His Leu Pro Asn Leu Thr Glu Glu Gln Arg
    130                 135                 140

Asn Ala Phe Ile Gln Ser Leu Lys Asp Asp Pro Ser Val Ser Lys Glu
145                 150                 155                 160

Ile Leu Ala Glu Ala Lys Lys Leu Asn Asp Ala Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Thr Glu Glu Gln Arg Asn Ala Phe Ile Gln Ser
        195                 200                 205

Leu Lys Asp Asp Pro Ser Val Ser Lys Glu Ile Leu Ala Glu Ala Lys
    210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Ala Phe Ile Gln Ser Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys His His His His His Cys Lys Cys Cys
    290                 295                 300

<210> SEQ ID NO 16
```

<211> LENGTH: 301
<212> TYPE: PRT
<213> ORGANISM: Artificial Sequence
<220> FEATURE:
<223> OTHER INFORMATION: S41A (Z domain)

<400> SEQUENCE: 16

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
            20                  25                  30

Gln Ser Leu Lys Asp Asp Pro Ser Gln Ala Ala Asn Leu Leu Ala Glu
        35                  40                  45

Ala Lys Lys Leu Asn Asp Ala Gln Ala Pro Lys Val Asp Asn Lys Phe
    50                  55                  60

Asn Lys Glu Gln Gln Asn Ala Phe Tyr Glu Ile Leu His Leu Pro Asn
65                  70                  75                  80

Leu Asn Glu Glu Gln Arg Asn Ala Phe Ile Gln Ser Leu Lys Asp Asp
                85                  90                  95

Pro Ser Gln Ala Ala Asn Leu Leu Ala Glu Ala Lys Lys Leu Asn Asp
            100                 105                 110

Ala Gln Ala Pro Lys Val Asp Asn Lys Phe Asn Lys Glu Gln Gln Asn
        115                 120                 125

Ala Phe Tyr Glu Ile Leu His Leu Pro Asn Leu Asn Glu Glu Gln Arg
    130                 135                 140

Asn Ala Phe Ile Gln Ser Leu Lys Asp Asp Pro Ser Gln Ala Ala Asn
145                 150                 155                 160

Leu Leu Ala Glu Ala Lys Lys Leu Asn Asp Ala Gln Ala Pro Lys Val
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Ala Phe Ile Gln Ser
        195                 200                 205

Leu Lys Asp Asp Pro Ser Gln Ala Ala Asn Leu Leu Ala Glu Ala Lys
    210                 215                 220

Lys Leu Asn Asp Ala Gln Ala Pro Lys Val Asp Asn Lys Phe Asn Lys
225                 230                 235                 240

Glu Gln Gln Asn Ala Phe Tyr Glu Ile Leu His Leu Pro Asn Leu Asn
                245                 250                 255

Glu Glu Gln Arg Asn Ala Phe Ile Gln Ser Leu Lys Asp Asp Pro Ser
            260                 265                 270

Gln Ala Ala Asn Leu Leu Ala Glu Ala Lys Lys Leu Asn Asp Ala Gln
        275                 280                 285

Ala Pro Lys His His His His His Cys Lys Cys Cys
    290                 295                 300

<210> SEQ ID NO 17
<211> LENGTH: 301
<212> TYPE: PRT
<213> ORGANISM: Artificial Sequence
<220> FEATURE:
<223> OTHER INFORMATION: S41V (Z domain)

<400> SEQUENCE: 17

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile

-continued

```
                20                  25                  30
Gln Ser Leu Lys Asp Asp Pro Ser Gln Val Ala Asn Leu Leu Ala Glu
            35                  40                  45
Ala Lys Lys Leu Asn Asp Ala Gln Ala Pro Lys Val Asp Asn Lys Phe
         50                  55                  60
Asn Lys Glu Gln Gln Asn Ala Phe Tyr Glu Ile Leu His Leu Pro Asn
 65                  70                  75                  80
Leu Asn Glu Glu Gln Arg Asn Ala Phe Ile Gln Ser Leu Lys Asp Asp
                 85                  90                  95
Pro Ser Gln Ala Val Asn Leu Leu Ala Glu Ala Lys Lys Leu Asn Asp
            100                 105                 110
Ala Gln Ala Pro Lys Val Asp Asn Lys Phe Asn Lys Glu Gln Gln Asn
         115                 120                 125
Ala Phe Tyr Glu Ile Leu His Leu Pro Asn Leu Asn Glu Glu Gln Arg
     130                 135                 140
Asn Ala Phe Ile Gln Ser Leu Lys Asp Asp Pro Ser Gln Ala Val Asn
145                 150                 155                 160
Leu Leu Ala Glu Ala Lys Lys Leu Asn Asp Ala Gln Ala Pro Lys Val
                 165                 170                 175
Asp Asn Lys Phe Asn Lys Glu Gln Gln Asn Ala Phe Tyr Glu Ile Leu
             180                 185                 190
His Leu Pro Asn Leu Asn Glu Glu Gln Arg Asn Ala Phe Ile Gln Ser
         195                 200                 205
Leu Lys Asp Asp Pro Ser Gln Ala Val Asn Leu Leu Ala Glu Ala Lys
     210                 215                 220
Lys Leu Asn Asp Ala Gln Ala Pro Lys Val Asp Asn Lys Phe Asn Lys
225                 230                 235                 240
Glu Gln Gln Asn Ala Phe Tyr Glu Ile Leu His Leu Pro Asn Leu Asn
                 245                 250                 255
Glu Glu Gln Arg Asn Ala Phe Ile Gln Ser Leu Lys Asp Asp Pro Ser
             260                 265                 270
Gln Ala Val Asn Leu Leu Ala Glu Ala Lys Lys Leu Asn Asp Ala Gln
         275                 280                 285
Ala Pro Lys His His His His His His Cys Lys Cys Cys
     290                 295                 300

<210> SEQ ID NO 18
<211> LENGTH: 301
<212> TYPE: PRT
<213> ORGANISM: Artificial Sequence
<220> FEATURE:
<223> OTHER INFORMATION: N52L (Z domain)

<400> SEQUENCE: 18

Met Val Asp Asn Lys Phe Asn Lys Glu Gln Gln Asn Ala Phe Tyr Glu
 1               5                  10                  15
Ile Leu His Leu Pro Asn Leu Asn Glu Glu Gln Arg Asn Ala Phe Ile
                 20                  25                  30
Gln Ser Leu Lys Asp Asp Pro Ser Gln Ser Ala Asn Leu Leu Ala Glu
             35                  40                  45
Ala Lys Lys Leu Leu Asp Ala Gln Ala Pro Lys Val Asp Asn Lys Phe
         50                  55                  60
Asn Lys Glu Gln Gln Asn Ala Phe Tyr Glu Ile Leu His Leu Pro Asn
 65                  70                  75                  80
Leu Asn Glu Glu Gln Arg Asn Ala Phe Ile Gln Ser Leu Lys Asp Asp
```

```
                    85                  90                  95
Pro Ser Gln Ser Ala Asn Leu Leu Ala Glu Ala Lys Lys Leu Leu Asp
                100                 105                 110
Ala Gln Ala Pro Lys Val Asp Asn Lys Phe Asn Lys Glu Gln Gln Asn
                115                 120                 125
Ala Phe Tyr Glu Ile Leu His Leu Pro Asn Leu Asn Glu Glu Gln Arg
                130                 135                 140
Asn Ala Phe Ile Gln Ser Leu Lys Asp Asp Pro Ser Gln Ser Ala Asn
145                 150                 155                 160
Leu Leu Ala Glu Ala Lys Lys Leu Leu Asp Ala Gln Ala Pro Lys Val
                165                 170                 175
Asp Asn Lys Phe Asn Lys Glu Gln Gln Asn Ala Phe Tyr Glu Ile Leu
                180                 185                 190
His Leu Pro Asn Leu Asn Glu Glu Gln Arg Asn Ala Phe Ile Gln Ser
                195                 200                 205
Leu Lys Asp Asp Pro Ser Gln Ser Ala Asn Leu Leu Ala Glu Ala Lys
                210                 215                 220
Lys Leu Leu Asp Ala Gln Ala Pro Lys Val Asp Asn Lys Phe Asn Lys
225                 230                 235                 240
Glu Gln Gln Asn Ala Phe Tyr Glu Ile Leu His Leu Pro Asn Leu Asn
                245                 250                 255
Glu Glu Gln Arg Asn Ala Phe Ile Gln Ser Leu Lys Asp Asp Pro Ser
                260                 265                 270
Gln Ser Ala Asn Leu Leu Ala Glu Ala Lys Lys Leu Leu Asp Ala Gln
                275                 280                 285
Ala Pro Lys His His His His His Cys Lys Cys Cys
                290                 295                 300

<210> SEQ ID NO 19
<211> LENGTH: 301
<212> TYPE: PRT
<213> ORGANISM: Artificial Sequence
<220> FEATURE:
<223> OTHER INFORMATION: N52V (Z domain)

<400> SEQUENCE: 19

Met Val Asp Asn Lys Phe Asn Lys Glu Gln Gln Asn Ala Phe Tyr Glu
1               5                   10                  15
Ile Leu His Leu Pro Asn Leu Asn Glu Glu Gln Arg Asn Ala Phe Ile
                20                  25                  30
Gln Ser Leu Lys Asp Asp Pro Ser Gln Ser Ala Asn Leu Leu Ala Glu
                35                  40                  45
Ala Lys Lys Leu Val Asp Ala Gln Ala Pro Lys Val Asp Asn Lys Phe
50                  55                  60
Asn Lys Glu Gln Gln Asn Ala Phe Tyr Glu Ile Leu His Leu Pro Asn
65                  70                  75                  80
Leu Asn Glu Glu Gln Arg Asn Ala Phe Ile Gln Ser Leu Lys Asp Asp
                85                  90                  95
Pro Ser Gln Ser Ala Asn Leu Leu Ala Glu Ala Lys Lys Leu Val Asp
                100                 105                 110
Ala Gln Ala Pro Lys Val Asp Asn Lys Phe Asn Lys Glu Gln Gln Asn
                115                 120                 125
Ala Phe Tyr Glu Ile Leu His Leu Pro Asn Leu Asn Glu Glu Gln Arg
                130                 135                 140
Asn Ala Phe Ile Gln Ser Leu Lys Asp Asp Pro Ser Gln Ser Ala Asn
```

```
                145                 150                 155                 160
Leu Leu Ala Glu Ala Lys Lys Leu Val Asp Ala Gln Ala Pro Lys Val
                165                 170                 175

Asp Asn Lys Phe Asn Lys Glu Gln Gln Asn Ala Phe Tyr Glu Ile Leu
                180                 185                 190

His Leu Pro Asn Leu Asn Glu Glu Gln Arg Asn Ala Phe Ile Gln Ser
                195                 200                 205

Leu Lys Asp Asp Pro Ser Gln Ser Ala Asn Leu Leu Ala Glu Ala Lys
                210                 215                 220

Lys Leu Val Asp Ala Gln Ala Pro Lys Val Asp Asn Lys Phe Asn Lys
225                 230                 235                 240

Glu Gln Gln Asn Ala Phe Tyr Glu Ile Leu His Leu Pro Asn Leu Asn
                245                 250                 255

Glu Glu Gln Arg Asn Ala Phe Ile Gln Ser Leu Lys Asp Asp Pro Ser
                260                 265                 270

Gln Ser Ala Asn Leu Leu Ala Glu Ala Lys Lys Leu Val Asp Ala Gln
                275                 280                 285

Ala Pro Lys His His His His His His Cys Lys Cys Cys
                290                 295                 300

<210> SEQ ID NO 20
<211> LENGTH: 301
<212> TYPE: PRT
<213> ORGANISM: Artificial Sequence
<220> FEATURE:
<223> OTHER INFORMATION: S41A, N52V (Z domain)

<400> SEQUENCE: 20

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
                20                  25                  30

Gln Ser Leu Lys Asp Asp Pro Ser Gln Ala Ala Asn Leu Leu Ala Glu
                35                  40                  45

Ala Lys Lys Leu Val Asp Ala Gln Ala Pro Lys Val Asp Asn Lys Phe
50                  55                  60

Asn Lys Glu Gln Gln Asn Ala Phe Tyr Glu Ile Leu His Leu Pro Asn
65                  70                  75                  80

Leu Asn Glu Glu Gln Arg Asn Ala Phe Ile Gln Ser Leu Lys Asp Asp
                85                  90                  95

Pro Ser Gln Ala Ala Asn Leu Leu Ala Glu Ala Lys Lys Leu Val Asp
                100                 105                 110

Ala Gln Ala Pro Lys Val Asp Asn Lys Phe Asn Lys Glu Gln Gln Asn
                115                 120                 125

Ala Phe Tyr Glu Ile Leu His Leu Pro Asn Leu Asn Glu Glu Gln Arg
                130                 135                 140

Asn Ala Phe Ile Gln Ser Leu Lys Asp Asp Pro Ser Gln Ala Ala Asn
145                 150                 155                 160

Leu Leu Ala Glu Ala Lys Lys Leu Val Asp Ala Gln Ala Pro Lys Val
                165                 170                 175

Asp Asn Lys Phe Asn Lys Glu Gln Gln Asn Ala Phe Tyr Glu Ile Leu
                180                 185                 190

His Leu Pro Asn Leu Asn Glu Glu Gln Arg Asn Ala Phe Ile Gln Ser
                195                 200                 205

Leu Lys Asp Asp Pro Ser Gln Ala Ala Asn Leu Leu Ala Glu Ala Lys
```

```
                210                 215                 220
Lys Leu Val Asp Ala Gln Ala Pro Lys Val Asp Asn Lys Phe Asn Lys
225                 230                 235                 240

Glu Gln Gln Asn Ala Phe Tyr Glu Ile Leu His Leu Pro Asn Leu Asn
                245                 250                 255

Glu Glu Gln Arg Asn Ala Phe Ile Gln Ser Leu Lys Asp Asp Pro Ser
                260                 265                 270

Gln Ala Ala Asn Leu Leu Ala Glu Ala Lys Lys Leu Val Asp Ala Gln
                275                 280                 285

Ala Pro Lys His His His His His Cys Lys Cys Cys
                290                 295                 300

<210> SEQ ID NO 21
<211> LENGTH: 301
<212> TYPE: PRT
<213> ORGANISM: Artificial Sequence
<220> FEATURE:
<223> OTHER INFORMATION: S41V, N52V (Z domain)

<400> SEQUENCE: 21

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
                20                  25                  30

Gln Ser Leu Lys Asp Asp Pro Ser Gln Val Ala Asn Leu Leu Ala Glu
                35                  40                  45

Ala Lys Lys Leu Val Asp Ala Gln Ala Pro Lys Val Asp Asn Lys Phe
50                  55                  60

Asn Lys Glu Gln Gln Asn Ala Phe Tyr Glu Ile Leu His Leu Pro Asn
65                  70                  75                  80

Leu Asn Glu Glu Gln Arg Asn Ala Phe Ile Gln Ser Leu Lys Asp Asp
                85                  90                  95

Pro Ser Gln Val Ala Asn Leu Leu Ala Glu Ala Lys Lys Leu Val Asp
                100                 105                 110

Ala Gln Ala Pro Lys Val Asp Asn Lys Phe Asn Lys Glu Gln Gln Asn
                115                 120                 125

Ala Phe Tyr Glu Ile Leu His Leu Pro Asn Leu Asn Glu Glu Gln Arg
                130                 135                 140

Asn Ala Phe Ile Gln Ser Leu Lys Asp Asp Pro Ser Gln Val Ala Asn
145                 150                 155                 160

Leu Leu Ala Glu Ala Lys Lys Leu Val Asp Ala Gln Ala Pro Lys Val
                165                 170                 175

Asp Asn Lys Phe Asn Lys Glu Gln Gln Asn Ala Phe Tyr Glu Ile Leu
                180                 185                 190

His Leu Pro Asn Leu Asn Glu Glu Gln Arg Asn Ala Phe Ile Gln Ser
                195                 200                 205

Leu Lys Asp Asp Pro Ser Gln Val Ala Asn Leu Leu Ala Glu Ala Lys
                210                 215                 220

Lys Leu Val Asp Ala Gln Ala Pro Lys Val Asp Asn Lys Phe Asn Lys
225                 230                 235                 240

Glu Gln Gln Asn Ala Phe Tyr Glu Ile Leu His Leu Pro Asn Leu Asn
                245                 250                 255

Glu Glu Gln Arg Asn Ala Phe Ile Gln Ser Leu Lys Asp Asp Pro Ser
                260                 265                 270

Gln Val Ala Asn Leu Leu Ala Glu Ala Lys Lys Leu Val Asp Ala Gln
```

```
                    275                 280                 285
Ala Pro Lys His His His His His Cys Lys Cys Cys
    290                 295                 300

<210> SEQ ID NO 22
<211> LENGTH: 301
<212> TYPE: PRT
<213> ORGANISM: Artificial Sequence
<220> FEATURE:
<223> OTHER INFORMATION: S41A, V52L (Z domain)

<400> SEQUENCE: 22

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
            20                  25                  30

Gln Ser Leu Lys Asp Asp Pro Ser Gln Ala Ala Asn Leu Leu Ala Glu
        35                  40                  45

Ala Lys Lys Leu Leu Asp Ala Gln Ala Pro Lys Val Asp Asn Lys Phe
    50                  55                  60

Asn Lys Glu Gln Gln Asn Ala Phe Tyr Glu Ile Leu His Leu Pro Asn
65                  70                  75                  80

Leu Asn Glu Glu Gln Arg Asn Ala Phe Ile Gln Ser Leu Lys Asp Asp
                85                  90                  95

Pro Ser Gln Ala Ala Asn Leu Leu Ala Glu Ala Lys Lys Leu Leu Asp
            100                 105                 110

Ala Gln Ala Pro Lys Val Asp Asn Lys Phe Asn Lys Glu Gln Gln Asn
        115                 120                 125

Ala Phe Tyr Glu Ile Leu His Leu Pro Asn Leu Asn Glu Glu Gln Arg
    130                 135                 140

Asn Ala Phe Ile Gln Ser Leu Lys Asp Asp Pro Ser Gln Ala Ala Asn
145                 150                 155                 160

Leu Leu Ala Glu Ala Lys Lys Leu Leu Asp Ala Gln Ala Pro Lys Val
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Ala Phe Ile Gln Ser
        195                 200                 205

Leu Lys Asp Asp Pro Ser Gln Ala Ala Asn Leu Leu Ala Glu Ala Lys
    210                 215                 220

Lys Leu Leu Asp Ala Gln Ala Pro Lys Val Asp Asn Lys Phe Asn Lys
225                 230                 235                 240

Glu Gln Gln Asn Ala Phe Tyr Glu Ile Leu His Leu Pro Asn Leu Asn
                245                 250                 255

Glu Glu Gln Arg Asn Ala Phe Ile Gln Ser Leu Lys Asp Asp Pro Ser
            260                 265                 270

Gln Ala Ala Asn Leu Leu Ala Glu Ala Lys Lys Leu Leu Asp Ala Gln
        275                 280                 285

Ala Pro Lys His His His His His Cys Lys Cys Cys
    290                 295                 300

<210> SEQ ID NO 23
<211> LENGTH: 18
<212> TYPE: PRT
<213> ORGANISM: Bacillus stearothermophilus

<400> SEQUENCE: 23
```

Glu Ala Gln Lys Gln Lys Glu Gln Arg Gln Ala Ala Glu Glu Leu Ala
1               5                   10                  15

Asn Ala

<210> SEQ ID NO 24
<211> LENGTH: 20
<212> TYPE: PRT
<213> ORGANISM: Homo Sapiens

<400> SEQUENCE: 24

Thr Ser Asp Tyr Ser Lys Tyr Leu Asp Ser Arg Arg Ala Gln Asp Phe
1               5                   10                  15

Val Gln Trp Leu
            20

<210> SEQ ID NO 25
<211> LENGTH: 23
<212> TYPE: PRT
<213> ORGANISM: Paramecium tetraurelia

<400> SEQUENCE: 25

Phe Leu Ser Leu Met Ala Arg Lys Met Lys Glu Gln Asp Ser Glu Glu
1               5                   10                  15

Glu Leu Ile Glu Ala Phe Lys
            20

<210> SEQ ID NO 26
<211> LENGTH: 27
<212> TYPE: PRT
<213> ORGANISM: Homo Sapiens

<400> SEQUENCE: 26

Glu Ile Asp Ser Thr Trp Ser Ala Leu Glu Lys Ala Glu Gln Glu His
1               5                   10                  15

Ala Glu Ala Leu Arg Ile Glu Leu Lys Arg Gln
            20                  25

<210> SEQ ID NO 27
<211> LENGTH: 75
<212> TYPE: PRT
<213> ORGANISM: Homo Sapiens

<400> SEQUENCE: 27

Glu Gly Glu Tyr Ile Lys Leu Lys Val Ile Gly Gln Asp Ser Ser Glu
1               5                   10                  15

Ile His Phe Lys Val Lys Met Thr Thr His Leu Lys Lys Leu Lys Glu
                20                  25                  30

Ser Tyr Cys Gln Arg Gln Gly Val Pro Met Asn Ser Leu Arg Phe Leu
            35                  40                  45

Phe Glu Gly Gln Arg Ile Ala Asp Asn His Thr Pro Lys Glu Leu Gly
        50                  55                  60

Met Glu Glu Glu Asp Val Ile Glu Val Tyr Gln
65                  70                  75

<210> SEQ ID NO 28
<211> LENGTH: 48
<212> TYPE: PRT
<213> ORGANISM: Homo Sapiens

<400> SEQUENCE: 28

```
Asn Ser Tyr Pro Gly Cys Pro Ser Ser Tyr Asp Gly Tyr Cys Leu Asn
1               5                   10                  15

Gly Gly Val Cys Met His Ile Glu Ser Leu Asp Ser Tyr Thr Cys Asn
            20                  25                  30

Cys Val Ile Gly Tyr Ser Gly Asp Arg Cys Gln Thr Arg Asp Leu Arg
            35                  40                  45
```

<210> SEQ ID NO 29
<211> LENGTH: 40
<212> TYPE: PRT
<213> ORGANISM: Homo Sapiens

<400> SEQUENCE: 29

```
Ser Glu Tyr Glu Thr Met Leu Thr Glu Ile Met Ser Met Gly Tyr Glu
1               5                   10                  15

Arg Glu Arg Val Val Ala Ala Leu Arg Ala Ser Tyr Asn Asn Pro His
            20                  25                  30

Arg Ala Val Glu Tyr Leu Leu Thr
            35                  40
```

<210> SEQ ID NO 30
<211> LENGTH: 58
<212> TYPE: PRT
<213> ORGANISM: Artificial Sequence
<220> FEATURE:
<223> OTHER INFORMATION: 9B domain

<400> SEQUENCE: 30

```
Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Gln Ala Lys Glu Ile Leu Ala Glu Ala
            35                  40                  45

Lys Lys Leu Asn Asp Ala Gln Ala Pro Lys
            50                  55
```

<210> SEQ ID NO 31
<211> LENGTH: 58
<212> TYPE: PRT
<213> ORGANISM: Artificial Sequence
<220> FEATURE:
<223> OTHER INFORMATION: 9F domain

<400> SEQUENCE: 31

```
Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Gln Leu Lys Glu Ile Leu Ala Glu Ala
            35                  40                  45

Lys Lys Leu Asn Asp Ala Gln Ala Pro Lys
            50                  55
```

<210> SEQ ID NO 32
<211> LENGTH: 58
<212> TYPE: PRT
<213> ORGANISM: Artificial Sequence
<220> FEATURE:
<223> OTHER INFORMATION: 8E domain

<400> SEQUENCE: 32

```
Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Gln Lys Phe Ile Gln
                20                  25                  30

Ser Leu Lys Asp Asp Pro Ser Gln Ala Lys Glu Ile Leu Ala Glu Ala
            35                  40                  45

Lys Lys Leu Val Asp Ala Gln Ala Pro Lys
        50                  55

<210> SEQ ID NO 33
<211> LENGTH: 58
<212> TYPE: PRT
<213> ORGANISM: Artificial Sequence
<220> FEATURE:
<223> OTHER INFORMATION: 8C domain

<400> SEQUENCE: 33

Val Asp Asn Lys Phe Asn Lys Glu Gln Gln Asn Ala Phe Tyr Glu Ile
1               5                   10                  15

Leu His Leu Pro Asn Leu Thr Glu Gln Arg Asn Lys Phe Ile Gln
                20                  25                  30

Ser Leu Lys Asp Asp Pro Ser Gln Ser Lys Glu Ile Leu Ala Glu Ala
            35                  40                  45

Lys Lys Leu Asn Asp Ala Gln Ala Pro Lys
        50                  55
```

ALKALI-TOLERANT AFFINITY CHROMATOGRAPHY LIGANDS

CLAIM OF PRIORITY

This application claims priority under 35 USC § 119(e) to U.S. Patent Application Ser. No. 62/966,743, filed on Jan. 28, 2020 and U.S. Patent Application Ser. No. 62/870,314, filed on Jul. 3, 2019, the entire contents of which are hereby incorporated by reference.

STATEMENT REGARDING SEQUENCE LISTING

The Sequence Listing associated with this application is provided in text form in lieu of a paper copy, and is hereby incorporated by reference into the specification. The name of the text file containing the Sequence Listing is Sequence-Listing.txt. The text file is 36.3 KB, and was created on Sep. 30, 2020.

TECHNICAL FIELD

This disclosure generally relates to affinity chromatography ligands and methods of making and using the affinity chromatography ligands.

BACKGROUND

Affinity chromatography is a method of separating a population of molecules of interest from a mixture based on interaction between a ligand (i.e. affinity ligand) and the molecules of interest. The affinity ligand is typically immobilized on a solid support to form a stationary phase. A mobile phase, which contains the molecules of interest, passes through the stationary phase. Because of the specific interaction, the molecules of interest can bind to the stationary phase. Finally, an elution process is applied to release the bound molecules from the stationary phase. Affinity chromatography is often a preferred method for isolating bioproducts.

In modern biotech and pharmaceutical industries, in order to reduce the cost, it is often important to reuse the affinity chromatography ligands. Thus, there is a need to develop affinity chromatography ligands that can be reused multiple times.

SUMMARY

This disclosure relates to chromatography ligands comprising one or more domains of Staphylococcal Protein A (SPA), or any functional variants thereof, as well as methods of making and using the same.

In some aspects, the disclosure relates to a polypeptide comprising an immunoglobulin (Ig)-binding domain. In some embodiments, the Ig-binding domain comprises an amino acid sequence that is at least 60% identical to SEQ ID NO: 6. In some embodiments, either one or both of the amino acids that correspond to S41 and N52 of SEQ ID NO: 6 are hydrophobic.

In some embodiments, the amino acid sequence meets one of the following conditions:
(1) the amino acid sequence is at least 80% identical to SEQ ID NO: 1, wherein either one or both of the amino acids that correspond to S44 and N55 of SEQ ID NO: 1 are hydrophobic;
(2) the amino acid sequence is at least 80% identical to SEQ ID NO: 2, wherein either one or both of the amino acids that correspond to S43 and N54 of SEQ ID NO: 2 are hydrophobic;
(3) the amino acid sequence is at least 80% identical to SEQ ID NO: 3, wherein either one or both of the amino acids that correspond to S41 and N52 of SEQ ID NO: 3 are hydrophobic;
(4) the amino acid sequence is at least 80% identical to SEQ ID NO: 4, wherein either one or both of the amino acids that correspond to S41 and N52 of SEQ ID NO: 4 are hydrophobic;
(5) the amino acid sequence is at least 80% identical to SEQ ID NO: 5, wherein either one or both of the amino acids that correspond to S41 and N52 of SEQ ID NO: 5 are hydrophobic; or
(6) the amino acid sequence is at least 80% identical to SEQ ID NO: 6, wherein either one or both of the amino acids that correspond to S41 and N52 of SEQ ID NO: 6 are hydrophobic.

In some embodiments, the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 is hydrophobic.

In some embodiments, the amino acid that corresponds to N55 of SEQ ID NO: 1, N54 of SEQ ID NO: 2, N52 of SEQ ID NO: 3, N52 of SEQ ID NO: 4, N52 of SEQ ID NO: 5 or N52 of SEQ ID NO: 6 is hydrophobic.

In some embodiments, both (1) the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 and (2) the amino acid that corresponds to N55 of SEQ ID NO: 1, N54 of SEQ ID NO: 2, N52 of SEQ ID NO: 3, N52 of SEQ ID NO: 4, N52 of SEQ ID NO: 5 or N52 of SEQ ID NO: 6 are hydrophobic.

In some embodiments, the Ig-binding domain comprises one of the following amino acid sequences:
(1) an amino acid sequence that is identical to SEQ ID NO: 1, except that either one or both of the amino acids at position 44 and position 55 of SEQ ID NO: 1 are hydrophobic;
(2) an amino acid sequence that is identical to SEQ ID NO: 2, except that either one or both of the amino acids at position 43 and position 54 of SEQ ID NO: 2 are hydrophobic;
(3) an amino acid sequence that is identical to SEQ ID NO: 3, except that either one or both of the amino acids at position 41 and position 52 of SEQ ID NO: 3 are hydrophobic;
(4) an amino acid sequence that is identical to SEQ ID NO: 4, except that either one or both of the amino acids at position 41 and position 52 of SEQ ID NO: 4 are hydrophobic;
(5) an amino acid sequence that is identical to SEQ ID NO: 5, except that either one or both of the amino acids at position 41 and position 52 of SEQ ID NO: 5 are hydrophobic;
(6) an amino acid sequence that is identical to SEQ ID NO: 6, except that either one or both of the amino acids at position 41 and position 52 of SEQ ID NO: 6 are hydrophobic.

In some embodiments, the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 is Ala, Val, Ile, Leu, Met, Phe, Try, or Trp.

In some embodiments, the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 is Ala or Val.

In some embodiments, the amino acid that corresponds to N55 of SEQ ID NO: 1, N54 of SEQ ID NO: 2, N52 of SEQ ID NO: 3, N52 of SEQ ID NO: 4, N52 of SEQ ID NO: 5 or N52 of SEQ ID NO: 6 is Ala, Val, Ile, Leu, Met, Phe, Try, or Trp.

In some embodiments, the amino acid that corresponds to N55 of SEQ ID NO: 1, N54 of SEQ ID NO: 2, N52 of SEQ ID NO: 3, N52 of SEQ ID NO: 4, N52 of SEQ ID NO: 5 or N52 of SEQ ID NO: 6 is Ala or Val.

In some embodiments, the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 is Ala and the amino acid that corresponds to N55 of SEQ ID NO: 1, N54 of SEQ ID NO: 2, N52 of SEQ ID NO: 3, N52 of SEQ ID NO: 4, N52 of SEQ ID NO: 5 or N52 of SEQ ID NO: 6 is Val.

In some embodiments, the amino acid sequence comprises a sequence that is at least 80%, 85%, 90%, 95%, or 100% identical SEQ ID NO: 11, 30, 31, or 32.

In some embodiments, the polypeptide comprises at least 2, 3, 4, or 5 Ig-binding domains.

In some embodiments, each Ig-binding domain comprises an amino acid sequence that is at least 80% identical to any one of SEQ ID NOS: 1-6.

In some embodiments, the polypeptide comprises 5 Ig-binding domains. In some embodiments, each Ig-binding domain comprises an amino acid sequence that is at least 80% identical to SEQ ID NO: 6, and either one or both of the amino acids that correspond to S41 and N52 of SEQ ID NO: 6 in each Ig-binding domain are hydrophobic.

In some embodiments, at least two Ig-binding domains are identical. In some embodiments, at least two Ig-binding domains are different.

In some embodiments, at least two neighboring Ig-binding domains are separated by at least one spacer domain. In some embodiments, the spacer domain comprises an alpha helix, a helix bundle, or a L9 connecting helix.

In some aspects, the disclosure relates to a vector comprising a polynucleotide encoding the polypeptide as described herein.

In some aspect, the disclosure relates to a chromatography ligand comprising the polypeptide as described herein.

In some embodiments, the chromatography ligand is immobilized on a solid support. In some embodiments, the solid support is selected from the group consisting of polysaccharides (e.g., agarose, cellulose, dextran, alginate, or starch), co-polymers, natural or synthetic polymers, silica, glass, plastic, metal and ceramics. In some embodiments, the solid support is in the form of micro-bead, nano-bead, membrane, hydrogel or fiber.

In some embodiments, the chromatography ligand retains at least about 70%, 75%, 80%, 85%, 90% or 95% of Ig-binding capacity after 24 hours of incubation in a 0.5 M NaOH solution. In some embodiments, the chromatography ligand retains at least about 70%, 75%, 80%, 85%, 90% or 95% of Ig-binding capacity after 24 hours to 36 hours of incubation in a 0.5 M NaOH solution.

In some aspects, the disclosure relates to an affinity chromatography matrix, comprising a plurality of the polypeptide as described herein. In some embodiments, the polypeptide is covalently coupled to a solid support. In some embodiments, the solid support is selected from the group consisting of polysaccharides (e.g., agarose, cellulose, dextran, alginate, starch), co-polymers, natural or synthetic polymers, silica, glass, plastic, metal and ceramics. In some embodiments, the solid support is in the form of micro-bead, nano-bead, membrane, hydrogel or fiber.

In some embodiments, the matrix retains at least about 70%, 75%, 80%, 85%, 90% or 95% of Ig-binding capacity after 24 hours of incubation in a 0.5 M NaOH solution. In some embodiments, the matrix retains at least about 70%, 75%, 80%, 85%, 90% or 95% of Ig-binding capacity after 24 hours to 36 hours of incubation in a 0.5 M NaOH solution.

In one aspect, the present disclosure provides a variant of a SPA Ig-binding domain, wherein at least one hydrophilic residue of the SPA Ig-binding domain is substituted with a hydrophobic residue. In some embodiments, the hydrophilic residue is a Serine (Ser) or an Asparagine (Asn), whereas the hydrophobic reside is selected from the group consisting of Ala, Val, Ile, Leu, Met, Tyr, Phe and Trp.

In some embodiments, the present disclosure provides an affinity ligand, which comprises one or more of variants of SPA Ig-binding domains as described herein. In some embodiments, the affinity ligand exhibits extremely high alkali-tolerance and can retain its Ig-binding capability after being treated by alkali.

In some embodiments, the present disclosure also provides an affinity chromatography medium, which comprises the variants of SPA Ig-binding domains as the affinity ligands and a solid supporting matrix.

In one aspect, the disclosure relates to an immunoglobulin (Ig)-binding protein with improved alkali-tolerance having affinity for immunoglobulin molecules of IgG, IgA and IgM, comprising one or more Ig-binding domains derived from Ig-binding domains of E (SEQ ID NO: 1), D (SEQ ID NO: 2), A (SEQ ID NO: 3), B (SEQ ID NO: 4), C (SEQ ID NO: 5) or Z (SEQ ID NO: 6) of Staphylococcus aureus Protein A or any functional fragments or variants thereof. In some embodiments, one or both amino acid residues at the position R1 and R2 are mutated to a hydrophobic residue selected from the group consisting of Ala, Val, Ile, Leu, Met, Phe, Tyr and Trp.

In some embodiments, the position R1 is a conserved residue corresponding to Ser41 of domain A (SEQ ID NO: 3), Ser41 of domain B (SEQ ID NO: 4), Ser41 of domain C (SEQ ID NO: 5) Ser41 of domain Z (SEQ ID NO: 6), Ser44 of domain E (SEQ ID NO: 1), or Ser43 of domain D (SEQ ID NO: 2), or the equivalent Serine residue in any functional variants of domain A, B, C, D, E and Z.

In some embodiments, the position R2 is a conserved residue corresponding to the Asn52 of domain A (SEQ ID NO: 3), Asn52 of domain B (SEQ ID NO: 4), Asn52 of domain C (SEQ ID NO: 5), Asn52 of domain Z (SEQ ID NO: 6), Asn55 of domain E (SEQ ID NO: 1), or Asn54 of domain D (SEQ ID NO: 2), or the equivalent Asparagine residue in any functional variants of domain A, B, C, D, Z and E.

In some embodiments, the sequence of the protein can comprise two or more identical Ig-binding domains. In some embodiments, the sequence of the protein can comprise two or more different Ig-binding domains.

In some embodiments, the sequence of the protein can comprise one or more additional residues or sequences, which are not part of the Ig-binding domains.

In one aspect, the disclosure relates to an affinity chromatography matrix, comprising a plurality of the Ig-binding proteins as described herein. In some embodiments, the Ig-binding proteins are covalently coupled to a solid support, wherein the solid support is selected from polysaccharides (including e.g., agarose, cellulose, dextran, alginate, starch and co-polymers), natural or synthetic polymers, silica, glass, plastic, metal or ceramics. In some embodiments, the solid support is in the form of micro-bead, nano-bead, membrane, hydrogel or fiber.

In some embodiments, the matrix retains about 80-100% of its original Ig-binding capacity after 24 hours of incubation in a 0.5 M NaOH solution.

In one aspect, the present disclosure relates to affinity ligands and the chromatography media comprising the affinity ligands as described herein. The affinity ligands are Ig-binding proteins that can have of one or more Ig-binding domains, and thus, have high affinity to immunoglobulin proteins including e.g., IgG and Fc-fusion proteins. The Ig-binding domains of the affinity ligands can be derived from the Ig-binding domains from Staphylococcus aureus Protein A (SPA), or any functional fragments or variants thereof. The present disclosure provides affinity ligands comprising the modified versions of the Ig-binding domains, which exhibit extraordinary alkali-tolerance.

As used herein, the term "about" refers to a deviation of +/−20%, preferably +/−10%, more preferably +/−5%, or even more preferably +/−1% of the measured numeric values, where applicable.

As used herein, the term "protein domain" or "domain" refers to a structurally stable unit or region of a protein. Unlike a random coil or a disordered loop, a domain has a stable and recognizable three-dimensional structure in non-denaturing conditions.

As used herein, the term "spacer domain" refers to a protein domain that separates two domains (e.g., immunoglobulins binding domains). A spacer domain is not a random coil or a disordered loop.

As used herein, the tem "Protein A immunoglobulin binding domain" or "SPA immunoglobulin binding domain" refer to an immunoglobulin binding domain of Staphylococcus Protein A (e.g., domains B, C, A, E, D), or the functional variants thereof (e.g., domain Z, domain $Z_{D36H}$).

As used herein, the terms "ligand" and "affinity ligand" are used interchangeably, and refer to a molecule which has specific binding capacity to another molecule.

As used herein, the term "chromatography" refers to a separation technique that utilizes the principles of chromatography, and includes e.g., batch, column as well as membrane-based chromatography.

As used herein, the term "affinity chromatography" refers to chromatography using affinity ligands to bind and purify target molecules.

As used herein, the terms "affinity medium" and "affinity matrix" are used interchangeably, and refer to a chromatography medium having a solid matrix and an affinity ligand that is immobilized on the solid matrix.

As used herein, the terms "solid support" and "solid matrix" are used interchangeably and refer to an insoluble material which is in the form of, without limitation, bead, membrane, tubing, porous particles, non-porous particle, monolithic gel, or fiber. In some embodiments, a solid support used for chromatography is commonly made with polysaccharides (e.g. agarose, cellulose, dextran, chitosan, and alginate), synthetic polymers (e.g. poly(methyl methacrylate)s (PMMA), poly(n-butyl methacrylate)s (PnBMA), and polystyrenes (PS)), magnetic metals, ceramics, silica, hydroxylapatite and/or zirconia-based materials.

As used herein, the term "couple/coupling/coupled" refers to a covalent linkage of a ligand molecule to a solid support.

As used herein, the term "immunoglobulin binding domain" refers to a domain that can bind to a constant region of immunoglobulins (e.g., Fc of IgG).

As used herein, the term "Fc" or "Fc-region" refers to the "fragment crystallizable" region of an immunoglobulin molecule.

As used herein, the term "Fe-binding domain" refers to a protein domain that has high affinity to the Fc-region of an immunoglobulin.

As used herein, the term "Protein A" or "SPA" refers to a 42 kDa surface protein encoded by the gene spa in Staphylococcus aureus. The Ig-binding domains of Protein A are also known as Fc-binding domains, including e.g., domain E (SEQ ID NO: 1), D (SEQ ID NO: 2), A (SEQ ID NO: 3), B (SEQ ID NO: 4) and C (SEQ ID NO: 5).

As used herein, the terms "Protein Z", "domain Z" and "Z domain" (SEQ ID NO: 6) are used interchangeably to refer a modified version of the domain B of Protein A.

As used herein, the term "functional variant" or "variant" of a protein or a protein domain refers to a variant protein or a variant protein domain, which retains essentially similar function of the protein or the protein domain (e.g., bind to Fc, effectively separate immunoglobulin binding domains). In some embodiments, the sequence of the functional variant of a protein or a protein domain has a sequence that is at least 70%, 80%, 90%, 95%, 96%, 97%, 98%, 99% identical to the protein or the protein domain.

As used herein, the term "non-Ig-binding region" refers to a segment of amino acid sequence that is outside of any Ig-binding domain (e.g., E, D, A, B, C, or Z domain) in the affinity ligand. A non-Ig-binding region does not have binding activity to an immunoglobulin molecule.

As used herein, the term "linker" refers to a segment of amino acid residues that connect two adjacent domains, or a segment of amino acid residues that is located at the termini of a polypeptide.

As used herein, the term "parent molecule" refers to a protein in the form before it is modified based on the methods described herein.

As used herein, the term "base" refers to a substance that release hydroxide (OH—) ions in aqueous solution. A basic solution has a pH of above 7.0. Hydroxide is a diatomic anion with chemical formula OH—. It consists of an oxygen and hydrogen atom held together by a covalent bond, and carries a negative electric charge. Some common bases include e.g., NaOH, KOH, and $NH_4OH$ (Ammonium hydroxide).

As used herein, the terms "alkali" refers to hydroxide of an alkali metal or alkaline earth metal. The alkali solution is a basic solution with a pH above 7.0. In some embodiments, the pH is above 8.0, preferably above pH 10.0, and more preferably above pH 12.0. Alkalis are all Arrhenius bases, which form hydroxide ions (OH—) when dissolved in water. Some common alkalis include e.g., NaOH, KOH, $Ca(OH)_2$, or $Mg(OH)_2$.

One important goal of the present disclosure is to provide an immunoglobulin (Ig)-binding protein, which retains its Ig-binding capacity after contacting a concentrated NaOH solution for a prolonged period. Such NaOH treatment is called Clean-in-Place (CIP). It is important because it can effectively remove the trace contaminants including host cell proteins, viruses, DNA, and other substances stuck on the matrix. This process is required before the affinity chromatography ligands or the chromatography medium comprising the affinity chromatography ligands can be reused. However, treating the affinity chromatography ligands with NaOH solution or other base can adversely affect the Ig-binding capacity of affinity chromatography ligands. To reduce the adverse effects, structure-based-protein-design has been employed to identify potential residues important for the structural stability of the Ig-binding domains of Staphylococcal Protein A (SPA) and a large number of SPA domains with various mutations were tested. The present disclosure provides after a large number of experiments and extensive modeling, that two amino acids as shown in FIG. 1 are in close proximity to the packing core of the Ig-binding domains, and mutating these amino acids to hydrophobic amino acids can significantly improve base-tolerance or alkali-tolerance (e.g., NaOH-tolerance). The present disclosure further shows that the affinity chromatography ligands comprising Ig-binding domains that have mutations at these positions have been determined to have excellent alkali-tolerance to sustain multiple Clean-In-Place (CIP) cycles.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 shows the sequence alignment of the Ig-binding domains (E, D, A, B, C and Z) of Staphylococcal Protein A. The sequences are set forth in SEQ ID NOS: 1-6. The two conserved hydrophilic residues at position R1 and R2 are highlighted.

FIG. 2 shows the 3D-stereo dispositions of the two key residues, R1 (Ser41 in domain B or the equivalent residue in the other domains) and R2 (Asn52 in domain B or the equivalent residue in the other domains). Each Ig-binding domain is packed into a three-helical bundle. The hydrophobic core of the domain is shown in stick-mode. The side chains of the two hydrophilic residues point to the hydrophobic core of the folded domain.

FIG. 8 shows the multi-sequence alignment result between domain Z (SEQ ID NO: 6), domain C (SEQ ID NO: 5), domain 9B (SEQ ID NO: 30), domain 9F (SEQ ID NO: 31), domain 8E (SEQ ID NO: 32) and domain 8C (SEQ ID NO: 33) using Clustal Omega.

FIG. 9 lists the several sequences as described in the present disclosure.

DETAILED DESCRIPTION

In the field of therapeutic antibodies, Protein A affinity chromatography is commonly used in the manufacturing processes. Protein A chromatography medium usually employs an Ig-binding protein as the ligand, which captures immunoglobulin (Ig) molecules. The Protein A ligand is derived from the Staphylococcus aureus Protein A (SPA). The native SPA is a cell-wall anchored 42 kDa protein, containing five Ig-binding domains (designated as domain E (SEQ ID NO: 1), domain D (SEQ ID NO: 2), domain A (SEQ ID NO: 3), domain B (SEQ ID NO: 4) and domain C (SEQ ID NO: 5)). The five Ig-binding domains are highly homologous and have similar Ig-binding capability. Among the five Ig-binding domains, the domain B and C are commonly used as chromatography ligands for antibody purification due to their high structural stability.

A single amino acid mutation G29A (i.e. Glycine residue at position 29 is substituted to Alanine) makes Domain B resistant to treatment with sodium hydroxide (NaOH) (Bjorn Nilsson, et. al. A synthetic IgG-binding domain based on staphylococcal protein A. Protein Engineering vol. 1 no. 2 pp. 107-113, 1987). This modified domain B is usually called domain Z (SEQ ID NO: 6). The sequence of domain Z is shown in FIG. 1. Domain C, which is also resistant to NaOH treatment, is also commonly used in antibody purification. Domain C and functional fragments or variants thereof are described, e.g., in U.S. Pat. No. 8,329,860, which is incorporated by reference in its entirety.

The recombinant domain B, domain Z, domain C or their functional variants can be used as chromatography ligands. The ligands usually have multiple Ig-binding domains in tandem. Most commercially available SPA ligands have 4 or 5 repeating domains in series, and each ligand can accommodate about 2 IgG molecules in solution. Each IgG binding domain of SPA has a compact 3-helical structure with only a few non-helical residues at the ends.

During industrial production of therapeutic antibodies, the SPA matrix is often recycled to minimize production cost. For each cycle of reuse, the SPA matrix is treated with a concentrated NaOH solution to effectively remove trace contaminants including host cell proteins, viruses, DNA, and other substances stuck on the matrix. Such NaOH treatment is called Clean-in-Place (CIP) when the SPA matrix is kept in place (e.g., a column). A standard CIP procedure include e.g., treating the Protein A matrix with 0.1-0.5 M NaOH for 5 to 30 minutes (e.g., about 5, 10, 15, 20, 25, or 30 minutes). Therefore, a NaOH-tolerant or alkali-tolerant SPA ligand is very important for the industrial use.

Figure 3:
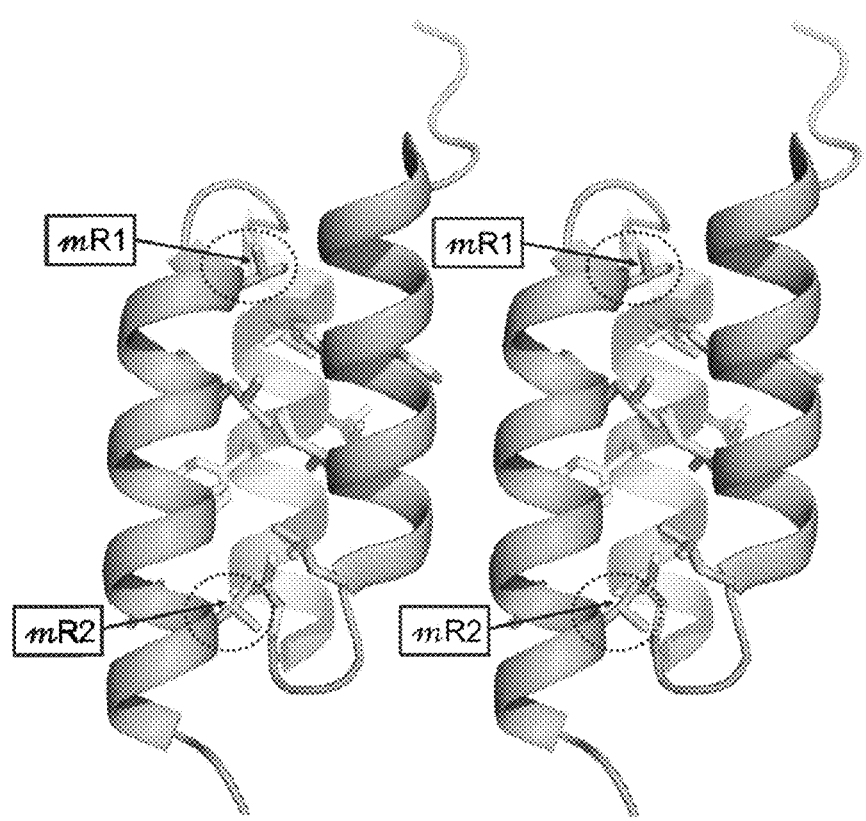
FIG. 3 shows a representative mutant form of IgG-binding domains of *Staphylococcal* Protein A after replacing the two conserved hydrophilic residues at R1 and R2 to two hydrophobic residues, respectively. The side chains of the two new hydrophobic residues face to the hydrophobic core of the protein. The increased hydrophobicity of the core would increase the packing stability of the three-helical bundle, resulting increased physical stability of the protein.

Extensive modeling has been performed to determine which amino acids are important for improving NaOH-tolerance or alkali-tolerance. Most of the proteins or individual domains have a hydrophobic core, which provides the structural stability of the protein. The residues of the hydrophobic core are generally not accessible to solvent and a polar surface in contact with the environment. In an aqueous environment, the initial interaction of those hydrophobic residues leads to the forming of a compact fold with well-defined secondary structures. The Levinthal's Principle infers that the protein folding process is not a random sampling of all possible conformational space, but rather specific pathways are initiated by native and non-native hydrophobic clusters of amino acid residues that maintain residual protein interactions even in denaturing environments (Levinthal, Cyrus (1969). "How to Fold Graciously". Mossbauer Spectroscopy in Biological Systems: Proceedings of a meeting held at Allerton House, Monticello, Ill.: 22-24). The structure shows that all the IgG-binding domains of SPA share the same hydrophobic core. Interestingly, there are two conserved hydrophilic residues having their side chains pointing to the hydrophobic core (FIG. 2). Structural analyses demonstrated that substitution of the two conserved hydrophilic residues to hydrophobic ones would decrease the free energy of the structure and thus increase the stability of the domains (FIG. 3).

The present disclosure is based on, in part, the observation from the structure analysis and experiment results that the amino acids at R1 and R2 (FIG. 1) (e.g., amino acids that correspond to S41 and N52 of Z domain (SEQ ID NO: 6)) are in close proximity to the packing core of the Ig-binding domains, and mutating these amino acids to hydrophobic amino acids can significantly improve alkali tolerance (e.g., NaOH-tolerance). Thus, the present disclosure provides various variants of SPA ligands that have improved alkali-resistance. These polypeptides can also be easily expressed in a recombinant expression system, thus are particularly suitable for industrial use.

Immunoglobulin Binding Domains

This disclosure provides chromatography ligands comprising one or more immunoglobulin binding domains. The term "immunoglobulin binding domain" refers to a domain that can bind to a constant region of immunoglobulins. Thus, the immunoglobulin binding domain can bind to immunoglobulins and also Fc-fusion proteins. In some embodiments, the immunoglobulin binding domain is an IgG binding domain.

The immunoglobulin binding domain in the chromatography ligands can be any immunoglobulin binding domain as described herein. For example, the immunoglobulin binding domain can be domains B, C, A, E, D derived from *Staphylococcus* Protein A, or their variants thereof. The immunoglobulin binding domains can also be domain Z or the variants thereof. The native SPA shows moderate alkali-tolerance. Among the five domains, domain B and C are commonly used as chromatography ligands due to their higher hydroxide-resistance. The domain Z is a functional variant of domain B of Protein A. Domain Z has a 3-helix bundle, which has about 58 amino acids. The Z domain (SEQ ID NO: 6), which have two point mutations (i.e. A1V and G29A as compared to B domain), exits higher alkali-tolerance than the parent molecule domain B. The present disclosure provides immunoglobulin binding domains with even higher alkali-tolerance.

The present disclosure relates to engineered immunoglobulin(Ig) binding domains (e.g., SPA immunoglobulin binding domains). The modifications on the SPA immunoglobulin binding domains can include point mutations, deletion or insertion. In some embodiments, the engineered immunoglobulin binding domains can be used as an affinity ligand for a chromatography medium for separation of immunoglobulins, e.g., IgG, IgA or IgM. In some embodiments, the engineered Ig-binding domains have higher alkali-tolerance than the Ig-binding domains without modifications as described herein (e.g., as compared to its parent version).

Extensive modeling shows that all Ig-binding domains of SPA share the same hydrophobic core. The hydrophobic core of a protein can maintain the structural integrity of the protein as a structurally stable protein or domain is usually folded against a hydrophobic core (Kalinowska et al. "Is the hydrophobic core a universal structural element in proteins?" Journal of molecular modeling 23.7 (2017): 205). The hydrophobic core of a protein remains folded or partially folded when the protein is contacting a denaturant such as alkali, acid, urea or guanidine. In other words, the hydrophobic core of a protein may resist a denaturant and maintain the structural integrity to a certain degree. During the refolding process of a denatured protein or domain in an aqueous solution, the hydrophobic core serves as the seed. Therefore, an intact hydrophobic core facilitates the folding process of a denatured protein. Strengthening the hydrophobicity of the core of a protein or domain will likely improve its folding/refolding capability.

All the five Ig-binding domains of SPA share the same structure as a three-helical bundle, which is folded against a hydrophobic core at the interface of the three helices (FIG. 2 and FIG. 3). Interestingly, the hydrophobic core of the SPA Ig-binding domains contains two conserved hydrophilic residues at the two ends (highlighted as R1 and R2 in FIG. 1). The two hydrophilic residues are Ser41 and Asn52 in domain A, B, C and Z, Ser44 and Asn55 in domain E or Ser43 and Asn54 in domain D. For the simplicity of the description, the two residues are named R1 and R2 in this disclosure (FIG. 1). Unlike other hydrophilic residues nearby, the side chains of R1 and R2 are pointing to the hydrophobic core without any ionic interactions with other surrounding residues. Point mutation of R1 and/or R2 with hydrophobic residues can increase the hydrophobicity of the core. The strengthened hydrophobicity of the folding core can enhance the structural stability of the SPA Ig-binding domains.

In some embodiments, the present disclosure provides several variants of an Ig-binding domain of SPA. At least one hydrophilic amino acid at R1 or R2 is mutated to a hydrophobic amino acid. The mutated domains showed increased alkali-tolerance than the parent version. As used herein, the term "hydrophobic amino acid" refers to an amino acid that has a side chain that is hydrophobic. Some common hydrophobic amino acids include e.g., Ala, Val, Ile, Leu, Met, Tyr, Phe and Trp.

In some embodiments, the mutated domain is modified from the B domain of SPA. In some embodiments, the mutated domain is modified from the Z domain. In some embodiments, the mutated domain is modified from the C domain of SPA. In some embodiments, the mutated domain is modified from the D domain of SPA. In some embodiments, the mutated domain is modified from the A domain of SPA. In some embodiments, the mutated domain is modified from the E domain of SPA.

In some embodiments, two conserved hydrophilic residues at R1 (Ser) and R2 (Asn) are mutated (FIG. 1). The two residues have their side chains pointing to the hydrophobic core of the helical bundle of the protein domain (FIG. 2). The two residues are located at the end of two helices, respectively, and their side chains of the R1 (Ser) and R2 (Asn) do not have hydrogen-bonding interaction with surrounding residues. Experiments show that mutation of the two residues will neither disrupt the structure of the helical bundle nor affect the Ig-binding capability of the domain.

In some aspects, the present disclosure provides an Ig-binding domain of SPA with one or more point mutations, wherein the R1 Serine residue is substituted with a hydrophobic residue (e.g., Ala, Val, Ile, Leu, Met, Tyr, Phe or Trp).

In some aspects, the present disclosure provides an Ig-binding domain of SPA with one or more point mutations, wherein the R2 Asparagine residue is substituted with a hydrophobic residue (e.g., Ala, Val, Ile, Leu, Met, Tyr, Phe or Trp).

In some aspects, the present disclosure provides an Ig-binding domain of SPA with two mutations, wherein the R1 Serine residue and R2 Asparagine residue are substituted with a hydrophobic residue (e.g., Ala, Val, Ile, Leu, Met, Tyr, Phe or Trp).

Thus, the present disclosure provides an engineered Ig-binding domain. In some embodiments, the Ig-binding domain comprises an amino acid sequence that is at least 60%, 70%, 75%, 80%, 85%, 90%, 91%, 92%, 93%, 94%, 95%, 96%, 97%, 98%, or 99% identical to SEQ ID NO: 1, wherein either one or both of the amino acids that correspond to S44 and N55 of SEQ ID NO: 1 are hydrophobic.

In some embodiments, the Ig-binding domain comprises an amino acid sequence that is at least 60%, 70%, 75%, 80%, 85%, 90%, 91%, 92%, 93%, 94%, 95%, 96%, 97%, 98%, or 99% identical to SEQ ID NO: 2, wherein either one or both of the amino acids that correspond to S43 and N54 of SEQ ID NO: 2 are hydrophobic.

In some embodiments, the Ig-binding domain comprises an amino acid sequence that is at least 60%, 70%, 75%, 80%, 85%, 90%, 91%, 92%, 93%, 94%, 95%, 96%, 97%, 98%, or 99% identical to SEQ ID NO: 3, wherein either one or both of the amino acids that correspond to S41 and N52 of SEQ ID NO: 3 are hydrophobic.

In some embodiments, the Ig-binding domain comprises an amino acid sequence that is at least 60%, 70%, 75%, 80%, 85%, 90%, 91%, 92%, 93%, 94%, 95%, 96%, 97%, 98%, or 99% identical to SEQ ID NO: 4, wherein either one or both of the amino acids that correspond to S41 and N52 of SEQ ID NO: 4 are hydrophobic.

In some embodiments, the Ig-binding domain comprises an amino acid sequence that is at least 60%, 70%, 75%, 80%, 85%, 90%, 91%, 92%, 93%, 94%, 95%, 96%, 97%, 98%, or 99% identical to SEQ ID NO: 5, wherein either one or both of the amino acids that correspond to S41 and N52 of SEQ ID NO: 5 are hydrophobic.

In some embodiments, the Ig-binding domain comprises an amino acid sequence that is at least 60%, 70%, 75%, 80%, 85%, 90%, 91%, 92%, 93%, 94%, 95%, 96%, 97%, 98%, or 99% identical to SEQ ID NO: 6, wherein either one or both of the amino acids that correspond to S41 and N52 of SEQ ID NO: 6 are hydrophobic.

As used herein, an amino acid in a sequence that "corresponds to" a reference amino acid in a reference sequence means an amino acid at the equivalent position after the sequence of interest and the reference sequence is aligned. In bioinformatics, the sequence alignment is often used to identify regions of similarity that may be a consequence of functional, structural, or evolutionary relationships between the sequences.

In some embodiments, the hydrophobic amino acids are Ala, Val, Ile, Leu, Met, Phe, Try, or Trp. In some embodiments, the hydrophobic amino acids are Ala or Val. In some embodiments, the hydrophobic amino acid is Leu.

In some embodiments, a mutant Ig-binding domain comprising mutations at R1 and/or R2 has higher alkali-tolerance than the parent molecule.

In some embodiments, domain Z can have one or more of the mutations selected from the group consisting of D36H, G9H, H18S, N23T, F30A, N28A, D36H, N3H, N6D and N23S. Thus, in some embodiments, the Ig-binding domains can have one or more additional mutations. For example, the amino acid in the Ig-binding domain that corresponds to D36 of Z domain (SEQ ID NO: 6) is H, G9 of Z domain is H, H18 of Z domain is S, N23 of Z domain is T, F30 of Z domain is A, N28 of Z domain is A, N3 of Z domain is H, N6 of Z domain is D and/or N23 of Z domain is S. In some embodies, the amino acid in the Ig-binding domain that corresponds to N3 of Z domain is H, N6 of Z domain is D and N23 of Z domain is S. In some embodies, the amino acid in the Ig-binding domain that corresponds to D36 of Z domain is H.

In some embodiments, a glycine linker (e.g., six glycine residues) can be inserted into the second loop of Z domain (Z (6G)).

In some embodiments, the conserved residue Gly29 on domain C can be mutated. Mutation of the Gly29 in domain C are described e.g., in EU patent 2412809 B1 and U.S. Pat. No. 9,403,883 B2, which are incorporated herein by reference in the entirety. Thus, in some embodiments, the amino acid in the Ig-binding domain that corresponds to G29 of C domain (SEQ ID NO: 5) is not Gly. In some embodiments, the amino acid in the Ig-binding domain that corresponds to G29 of C domain (SEQ ID NO: 5) is Ala. In some embodiments, the amino acid in the Ig-binding domain that corresponds to G29 of C domain (SEQ ID NO: 5) is Lys.

In some embodiments, the immunoglobulin binding domain is a fusion polypeptide of one or more of the immunoglobulin binding domain described herein (e.g., domains Z and domains C). In some embodiment, the N terminal portion is derived from Z domain (e.g., about or at least 20, 21, 22, 23, 24, 25, 26, 27, 28, 29, 30, 31, 32, 33, 34, 35, 36, 37, or 38 amino acids). In some embodiments, the C terminal portion is derived from C domain (e.g., about or at least 20, 21, 22, 23, 24, 25, 26, 27, 28, 29, 30, 31, 32, 33, 34, 35, 36, 37, or 38 amino acids). In some embodiments, the N terminal portion is derived from the first 28 amino acids of the N terminal of Z domain (SEQ ID NO: 6). In some embodiments, the C terminal portion is derived from that last 30 amino acids of the C terminal of C domain (SEQ ID NO: 5).

In some embodies, the amino acid in the Ig-binding domain that corresponds to N23 of Z domain (SEQ ID NO: 6) is Thr. In some embodies, the amino acid in the Ig-binding domain that corresponds to N28 of Z domain (SEQ ID NO: 6) is Gln. In some embodiments, the amino acid in the Ig-binding domain that corresponds to G29 of C domain (SEQ ID NO: 5) is Lys. In some embodiments, the amino acid in the Ig-binding domain that corresponds to V40 of C domain (SEQ ID NO: 5) is Gln. In some embodiments, the amino acid in the Ig-binding domain that corresponds to S41 of C domain (SEQ ID NO: 5) is Ala. In some embodiments, the amino acid in the Ig-binding domain that corresponds to N52 of C domain (SEQ ID NO: 5) is Val.

As used herein, a variant immunoglobulin binding domain can be a polypeptide that has a sequence that is at least 60%, 70%, 75%, 80%, 85%, 90%, 91%, 92%, 93%, 94%, 95%, 96%, 97%, 98%, or 99% identical to an immunoglobulin binding domains as described in this disclosure (e.g., domains B, C, A, E, D, Z, 9B, 9F, 8E or 8C). In some embodiments, the Ig-binding domain has a sequence that is identical to SEQ ID NO: 1, 2, 3, 4, 5, 6, 30, 31, 32, or 33 except the Ig-binding domain has mutations at R1 and/or R2 as described herein, or some other mutations as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Chromatography Ligands

The polypeptides can have one or more immunoglobulin binding domains. The chromatography ligands can have at least or about 1, 2, 3, 4, 5, 6, 7, 8, 9, 10 or more than 10 immunoglobulin binding domains as descried herein. In some embodiments, the IgG binding domains are connected continuously without additional linking sequences between the binding domains.

In some embodiments, the affinity ligand of can comprise 1 to 10, preferably 2 to 9, more preferably 3 to 8 and most preferably 4 to 7 Ig-binding domains, which are linked with or without additional linker region between any two neighboring domains. In some embodiments, the affinity ligand can comprise or consist of identical copies of a same domain. In some embodiments, the affinity ligand can comprise or consist of identical or different Ig-binding domains.

In some embodiments, the Ig-binding protein comprises at least 1, 2, 3, 4, 5, 6, 7, 8, 9, or 10 mutated Ig-binding domains with mutations as described herein. In some embodiments, each Ig-binding domain within the protein comprises at least one point mutation at R1 or R2 as described herein. In some embodiments, the affinity chromatography ligand comprises at least one modified Ig-binding domain having at least one point mutation at R1 or R2 as described herein.

In some embodiments, the Ig-binding affinity ligands have a sequence that is at least 70%, 75%, 80%, 85%, 90%, 91%, 92%, 93%, 94%, 95%, 96%, 97%, 98%, 99%, or 100% identical to SEQ ID NO: 7, 8, 9, 10, 11, 12, 13, 30, 31, 32 or 33. In some embodiments, at least 1, 2, 3, 4, or 5 Ig-binding domains in the affinity ligands have a mutation at R1 and/or R2.

In some embodiments, the chromatography ligand can be covalently attached to a solid support. The solid support can be micro-particles, nano-particles, hydrogel, monolithic gel, membrane, plastic, glass or metal surface, etc. In some embodiments, the Ig-binding affinity ligands can be covalently immobilized to the solid support in a single-attachment manner or in a multi-attachment manner.

In some embodiments, the engineered affinity ligand can also contain additional amino acids or sequence segments that are not related to the Ig-binding function. For example, an affinity tag or a linker region can be added to the terminal ends of the protein. In some embodiments, the engineered ligand can contain other modifications including but not limited to disulfide bonding, acetylation, glycosylation and conjugations with other molecules. In some embodiments, the chromatography ligands can have additional residues or components, e.g. a Cysteine residues or a poly-His tag. These additional residues or components can be used, e.g., for linking the chromatography ligand to a support matrix, solid surface or bead. Cysteine residues can be used for immobilization. Poly-His tags can be used for purifying chromatography ligands. Cysteine residues and poly-His tags are described, e.g., in Kimple, et al. "Overview of affinity tags for protein purification." Current Protocols in Protein Science (2004): 9-9; Magdeldin et al. "Affinity chromatography: Principles and applications." S. Magdeldin, InTech, Croatia (2012): 1-28; each of which is incorporated by reference in its entirety.

In some embodiments, the Ig-binding affinity ligand can retain 60% to 100%, preferably 70%-100%, more preferably 80%-100%, most preferably 90%-100% of its Ig-binding capability after contacting a 0.1-0.5 M alkali (e.g., NaOH) solution for a period of time (e.g., accumulatively 1, 2, 3, 4, 5, 6, 7, 8, 10, 12, 16, 18, 24, 35, 36, or 48 hours). In some embodiments, the period of time is at least 1, 2, 3, 4, 5, 6, 7, 8, 10, 12, 16, 18, 24, 35, 36, or 48 hours. In some embodiments, the period of time is less than 1, 2, 3, 4, 5, 6, 7, 8, 10, 12, 16, 18, 24, 35, 36, or 48 hours. In some embodiments, the Ig-binding affinity ligand can retain at least 70%, 75%, 80%, 85%, or 90% Ig-binding capability. In some embodiments, the concentration of alkali (e.g., NaOH) solution is about 0.1 M, 0.2 M, 0.3 M, 0.4 M or 0.5 M. In some embodiments, the concentration of alkali (e.g., NaOH) solution is at least 0.1 M, 0.2 M, 0.3 M, 0.4 M or 0.5 M.

The affinity ligands can have a high recovery yield for bound immunoglobulins (e.g., IgG). In some embodiments, the recovery yield is over 70%, 80%, 90%, 95%, 95%, 96%, 97%, 98%, or 99%. As used herein, the recovery yield refers to the percentage of immunoglobulins (e.g., IgG) that can be eluted at certain conditions out of the total amount immunoglobulins that can be eluted from chromatography. In some embodiments, the total amount immunoglobulins that can be eluted from chromatography is determined by the total amount of immunoglobulins that can be eluted at pH 2-3.

The recovery yield can be above 85%, 86%, 8'7%, 88%, 89%, 90%, 91%, 92%, 93%, 94%, 95%, 96%, 97%, 98%, or 99%. In some embodiments, the recovery yield is 85-99%, 90%-99%, or 95-99%.

The affinity ligands described herein can be expressed in a protein expression system such as *Pichia pastoris, E. coli* or any other appropriate expression system known in the art. In some embodiments, pET21a or pET28b vectors can be used to express the ligands. In some embodiments, the expressed affinity ligands can be purified by using chromatography techniques such as ionic exchanges, affinity, size exclusion and gel filtration. In some embodiments, the purified protein is buffer-exchanged to an amine-free and reducing-agent free buffer, which has about neutral pH. In some embodiments, the purified protein can be concentrated or diluted to an appropriate concentration, which is suitable for coupling to a solid support.

Spacer Domains

A spacer domain is a structurally stable protein domain, which has a folded three dimensional structure in aqueous solution. The spacer domain can physically separate neighboring immunoglobulin binding domains and serve as a spacer. In some embodiments, the spacer domain has more than 5, 6, 7, 8, 9, 10, 15, 20, 30, or 40 amino acid residues. In some embodiments, the spacer domain has less than 90, 80, 60, 50, 40, or 30 amino acid residues. In some embodiments, the length or diameter (e.g., maximum diameter when it is properly folded) of a spacer domain can be less than 60 Å, 50 Å, 40 Å, 30 Å, or 20 Å.

In some embodiments, the polypeptides have at least two immunoglobulin binding domains and at least one spacer domain, wherein every two neighboring immunoglobulin binding domains are separated by at least one spacer domain. In some embodiments, the polypeptides are fusion polypeptides. In some embodiments, the chromatography ligands can have multiple immunoglobulin binding domains, which are spatially separated by spacer domains.

A spacer domain, due to its structural rigidity, can physically separate the two neighboring immunoglobulin binding domains in solution. As used herein, the term "neighboring immunoglobulin binding domains" refers to two immunoglobulin binding domains that are close to each other, and they can be separated by spacer domains.

In some embodiments, the affinity ligand is a chimeric fusion protein comprising immunoglobulin binding domains (e.g., Ig binding domains) and non-Ig binding domains (e.g. spacer domains). In some embodiments, the fusion protein contains multiple copies of Ig binding domains. In some embodiments, the fusion protein contains multiple copies of non-Ig binding domains.

In some embodiments, the spacer domain is not a random coil or a disordered loop. In some embodiments, the spacer domain is not a random coil or a disordered loop at any elution pH described herein (e.g., about 3 to about 7, about 4 to about 7, about 4.5 to about 7).

One important aspect of the spacer domain is its structural stability. The structural stability refers to a well-defined tertiary structure under an appropriate range of conditions including pH, ionic strength, and buffer components in an aqueous solution for chromatography. In some embodiments, the structural stability also means the core of the spacer domain does not form a random coil structure in solution under a condition wherein the affinity ligand binds antibodies. The purpose of the spacer domain is to effectively keep some distance between the neighboring immunoglobulin domains.

In contrast, adding a flexible polypeptide linker between two protein domains is a common method for recombinant expression of a fusion protein or a chimeric protein. The linker is typically designed to be flexible, e.g. a mixture of Gly and Ser residues. These linkers usually cannot prevent the flanking domains from contacting with each other in a solution.

In some embodiments, the spacer domain is a small protein domain, which is about the same size as an immunoglobulin binding domain (e.g. Z domain). In some embodiments, the size of the S domain is similar or larger than a SPA immunoglobulin binding domain.

In some embodiments, the spacer domain is water soluble. In these cases, the amino acids that are exposed on the surface of spacer domain are preferably hydrophilic.

In some embodiments, the spacer domain can survive in strong acidic and strong basic conditions, thus have structural stability at low and high pH conditions. In some embodiments, the spacer domain can be easily re-folded to appropriate structure in neutral conditions after being denatured in extreme conditions (e.g., strong basic or acid solutions).

In some embodiments, the spacer domain is a single alpha helical domain. The single alpha helical domain is a good choice for spacer domain for several reasons. First, single alpha helical domains are the smallest domains that have stable structure. Second, they can easily be refolded after acid or base denaturing during purification process. Third, they have perfect N-C orientation to be integrated into the ligand. Finally, their size/length can be easily controlled as desired.

In some embodiments, the spacer domain can be the central connecting helix of ribosomal protein L9 from *B. stearothermophilus* (e.g., SEQ ID NO: 23). In some embodiments, the spacer domain can be a helical segment of glucagon (amino acids 7-26 of glucagon; e.g., SEQ ID NO: 24), connecting helix of calmodulin (amino acids 68-90 of calmodulin; e.g., SEQ ID NO: 25), or single alpha-helix domain (SAH) from Myosin-10 (amino acids 813-909 of Myosin-10; e.g., SEQ ID NO: 26). In some embodiments, the spacer domain is a small protein such as a Sumo domain (alpha helix and beta sheet; e.g., SEQ ID NO: 27), an EGF domain (beta sheet; e.g., SEQ ID NO: 28) or an ubiquitin-associated (UBA) domain of Rad23A (e.g., SEQ ID NO: 29).

In some embodiments, the spacer domain can be a peptide that has a sequence that is at least 70%, 80%, 90%, 95%, 96%, 97%, 98%, 99% identical to any spacer domain described in this disclosure.

In some embodiments, the spacer domain is a non-Ig binding domain. In some cases, the spacer domain does not have affinity to immunoglobulins or IgG. It does not affect the structural stability of the adjacent immunoglobulin binding domains and does not interfere with the refolding of the immunoglobulin binding domains after NaOH Cleaning in Place (CIP).

In some embodiments, the spacer domain does not interact with the neighboring immunoglobulin binding domains under physiological conditions or denaturing conditions (e.g., the spacer domain will not bind to the neighboring immunoglobulin binding domains, and will not block the binding between immunoglobulin binding domains and IgG). The spacer domain does not cause aggregation or denaturing of the immunoglobulin binding domains.

In some embodiments, the spacer domain is a folded protein domain, is a protein domain with three-dimensional structure, is a piece of alpha helix, is a helix bundle, is a beta-structure protein, is a mixed alpha-beta structure protein, or is a globular protein. In some cases, the spacer domain has no immunoglobulin binding affinity, is water soluble, is not a random coil in solution, is not a disordered loop in solution, and/or does not interfere with the function of Immunoglobulin binding domains.

Chromatography Matrix

The disclosure also provides a chromatography matrix for affinity separation of antibodies. The matrix can include affinity ligands that are covalently coupled to a solid support. The affinity ligands can be any affinity ligands described herein.

The solid support of the matrix can be made of any kind of suitable materials including polysaccharides (e.g., agarose, cellulose, starch, dextran), organic polymers (e.g., polyacrylamide, polyvinyl alcohol, polyhydroxyalkyl methacrylates) or inorganic aggregates (e.g., silica). The chromatography matrix can be in the form of beads (e.g., substantially spherical particles), a membrane, or monolithic gel. In some embodiments, the affinity ligands described herein can be covalently coupled to the matrix support in a single attachment style (e.g., with one attachment point). In some other cases, the affinity ligands can be covalently coupled to the support with multiple attachment points.

In some embodiments, the solid support is crosslinked agarose resin. In some embodiments, the agarose beads are activated with ethylene glycol diglycerol ether. For coupling of the ligands, the ligands as described herein are dissolved in a buffer and are then mixed with activated agarose beads. The coupled beads are then harvested. The remaining epoxy groups on the beads can be inactivated with ethaloamine. The beads are then further washed with deionized water before use.

In some embodiments, the affinity chromatography medium as described herein can be used for separation of IgG, IgA, IgM, or some other immunoglobulins, or fragments thereof. In some embodiments, the affinity chromatography medium as described herein can be used for purifying Fc-fusion proteins. An affinity chromatographic medium comprising a ligand and a solid support can have various forms, e.g., beads, membrane, hydrogel or nanoparticles. The solid support can be made with a variety of materials such as agarose, cellulose, dextran, silica, synthetic polymers, ceramics and metals. And the solid support can be coated, modified or conjugated with a variety of materials, which can provide conjugation sites for the affinity ligand to be immobilized.

In some embodiments, the affinity chromatography medium comprising the Ig-binding protein as described herein has superior alkali-tolerance. In some embodiments, the affinity chromatography medium can retain 60% to 100%, preferably 70%-100%, more preferably 80%400%, most preferably 90%400% of its Ig-binding capability after contacting a 0.1-0.5 M alkali (e.g., NaOH) solution for a period of time (e.g., accumulatively 1, 2, 3, 4, 5, 6, 7, 8, 10, 12, 16, 18, 24, 35, 36, or 48 hours). In some embodiments, the period of time is at least 1, 2, 3, 4, 5, 6, 7, 8, 10, 12, 16, 18, 24, 35, 36, or 48 hours. In some embodiments, the period of time is less than 1, 2, 3, 4, 5, 6, 7, 8, 10, 12, 16, 18, 24, 35, 36, or 48 hours. In some embodiments, the affinity chromatography medium can retain at least 70%, 75%, 80%, 85%, or 90% Ig-binding capability. In some embodiments, the concentration of alkali (e.g., NaOH) solution is about 0.1 M, 0.2 M, 0.3 M, 0.4 M or 0.5 M. In some embodiments, the concentration of alkali (e.g., NaOH) solution is at least 0.1 M, 0.2 M, 0.3 M, 0.4 M or 0.5 M.

In some embodiments, the percentages of remaining binding capability after alkali treatment is determined by dynamic binding capability (DBC). The dynamic binding capacity (DBC) can be calculated by the following equation:

$$DBC\ (mg/mL) = C_o \times (V_f - V_o)/CV,$$

wherein $C_o$ is the concentration of the antibody feedstock, Vi is the total volume of the injected sample up to the 10% break point, $V_0$ is the void volume from the injection point to the detector, and CV is the column volume. The 10% breakthrough point can be determined by e.g., the sharp turning of UV280 reading during column injection, wherein 10% of the maximum UV280 reading is reached.

In some embodiments, the DBC for affinity chromatography medium is at least 50, 55, 56, 57, 58, 59, 60, 61, 62, 63, 64, or 65 mg/ml before alkali (e.g., NaOH) treatment. In some embodiments, the DBC for affinity chromatography medium is at least 40, 41, 42, 43, 44, 45, 46, 47, 48, 49, 50, 51, 52, 53, 54, 55, 56, 57, 58, 59, 60, 61, 62, 63, 64, or 65 mg/ml after being treated by alkali (e.g., NaOH) for an extended period of time (e.g., accumulatively 1, 2, 3, 4, 5, 6, 7, 8, 10, 12, 16, 18, 24, 35, 36, or 48 hours). In some embodiments, the period of time is at least 1, 2, 3, 4, 5, 6, 7, 8, 10, 12, 16, 18, 24, 35, 36, or 48 hours. In some embodiments, the period of time is less than 1, 2, 3, 4, 5, 6, 7, 8, 10, 12, 16, 18, 24, 35, 36, or 48 hours.

In some embodiments, the chromatography medium has excellent alkali (e.g., NaOH) resistance, which is required for multiple round of CIP (Cleaning in Place). Thus, in some embodiments, the chromatography matrix coupled with the affinity ligands can be used in multiple cycles with CIP (e.g., cleaning with 0.1-0.5 M NaOH) treatment. The CIP treatment can effectively clean the chromatography medium without significantly affecting the binding capacity.

In some embodiments, the affinity chromatography medium can retain at least 70%, 75%, 80%, 85%, 90% or 95% of its Ig-binding capability (e.g., as measured by DBC) after several cycles of CIP (e.g., about or at least 20, 40, 60, 80, 100, 120, 140, 160, 180, or 200 cycles of CIP). In some embodiments, the affinity chromatography medium can retain at least 80% or 82% of its Ig-binding capability after 100 cycles of CIP. In some embodiments, each CIP cycle involves treating the chromatography medium with about 0.5M NaOH for about or at least 5, 10, 15. 20. 25, or 30 minutes (e.g., about or at least 15 minutes).

Chromatography Process

The chromatography matrix can be used to purify immunoglobulins, e.g., IgG, IgA, IgM, IgE, or fragments therefor. This disclosure also provides chromatography processes, wherein target immunoglobulins can be separated from a solution by binding to the chromatography matrix. As a skilled person in the field will easily understand, a solution denoted as an eluent is needed to pass through the affinity matrix to release or elute the bound protein on the matrix.

In some embodiments, the bound antibody (e.g., IgG) on the matrix is eluted by a solution with appropriate elution pH as described in this disclosure (e.g., pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, or pH 6.5, or in the range of pH 4.0 to pH 6.0).

In some embodiments, the chromatography ligands described herein allows the bound antibodies (e.g., IgG) to be eluted in relatively mild conditions, e.g., above pH 4.0, above pH 4.1, above pH 4.2, above pH 4.3, above pH 4.4, above pH 4.5, above pH 4.6, above pH 4.7, above pH 4.8, above pH 4.9, above pH 5.0, above pH 5.1, above pH 5.2, above pH 5.3, above pH 5.4, above pH 5.5, above pH 5.6, above pH 5.7, above pH 5.8, above pH 5.9, or above pH 6.0.

In some embodiments, the antibody is first bound to the affinity matrix. Solutions with a roughly linear gradient of pH from about pH 8.0 to about pH 3.0 is used to elute the bound antibody. Thus, in some embodiments the bound antibody (e.g., IgG) on the matrix are collected when the elution pH is in any appropriate pH ranges that are described in this disclosure (e.g., in the range of pH 4.0 to pH 6.0; or above pH 4.0, above pH 4.1, above pH 4.2, above pH 4.3, above pH 4.4, above pH 4.5, above pH 4.6, above pH 4.7, above pH 4.8, above pH 4.9, above pH 5.0, above pH 5.1, above pH 5.2, above pH 5.3, above pH 5.4, above pH 5.5, above pH 5.6, above pH 5.7, above pH 5.8, above pH 5.9, above pH 6.0, above pH 6.1, above pH 6.2, above pH 6.3, above pH 6.4, or above pH 6.5, with the maximum elution being pH 6.0, pH 6.1, pH 6.2, pH 6.3, pH 6.4, or pH 6.5).

In some other embodiment, a step-wise elution can be used. For example, a first buffer is used to wash the chromatography matrix, and a second buffer is used to elute immunoglobulins. The second buffer can have an appropriate pH as described in this disclosure (e.g., pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0). In some cases, a third buffer can be used to determine the total amount of antibodies that can be eluted from chromatography, which can be used for verification of total elution or yield. The pH for the third buffer should be lower than the pH of the second buffer (e.g., pH 2.0, pH 2.1, pH 2.2, pH 2.3, pH 2.4, pH 2.5, pH 2.6, pH 2.7, pH 2.8, pH 2.9, pH 3.0, or lower than pH 2.0).

The disclosure also provides methods of purifying immunoglobulins. The methods include the steps of contacting the chromatography ligands described herein with a solution comprising immunoglobulins; washing the chromatography ligand with a first buffer; and eluting the immunoglobulins with a second buffer having a selected pH. The selected pH can be any pH as described in this disclosure.

The disclosure also provides methods of purifying immunoglobulins. The methods include the steps of contacting the chromatography ligands described herein with a solution comprising immunoglobulins; washing the chromatography ligands with a buffer, wherein the buffer has a linear pH gradient over time; and collecting immunoglobulins in a selected pH. The linear pH gradient can be from about pH 8.0 to about pH 3.0. In some embodiments, the selected pH is from about 6.0 to about 4.0 (e.g., from about 6.0 to about 4.5, or from about 6.0 to about 4.7).

In some embodiments, the recovery yield at various described conditions can be greater than 50%, 60%, 70%, 80%, 90%, 95%, 96%, 97%, 98%, or 99%.

EXAMPLES

The invention is further described in the following examples, which do not limit the scope of the invention described in the claims.

Example 1: Mutagenesis of the Z Domain

Structure-based-protein-design was employed to identify potential residues important for the structural stability of the Ig-binding domains of *Staphylococcal* Protein A (SPA). About 12 mutants of the Z domain were tested for superior alkali-tolerance and high Ig-binding capability.

From the modeling and the experiments, R1 and R2 residues of the Ig-binding domains of SPA were identified to be important. These two residues were mutated to several representative hydrophobic amino acids. The Z domain with a single mutation at Ser 41 or Asn 52 and the Z domain with double mutations at Ser 41 and Asn 52 were designed. The mutations were listed in Table 1. The amino acid sequence of the wild type Z domain was set forth in SEQ ID NO: 6, and Z domain with mutations were listed in SEQ ID NOs: 7-13.

TABLE 1

Point mutations for the Z domain

| Mutants | Single mutation | Double mutations | SEQ ID NO |
|---|---|---|---|
| 1 | S41A | | 7 |
| 2 | S41V | | 8 |
| 3 | N52L | | 9 |
| 4 | N52V | | 10 |

TABLE 1-continued

Point mutations for the Z domain

| Mutants | Single mutation | Double mutations | SEQ ID NO |
|---|---|---|---|
| 5 | | S41A, N52V | 11 |
| 6 | | S41V, N52V | 12 |
| 7 | | S41A, V52L | 13 |

Example 2. Gene Synthesis for the Mutated Z Domains

The amino acid sequences of the Z domain variants were back-translated to DNA sequence. Codon optimization was performed for *E. coli* expression systems. A C domain mutant (C domain with G29A mutation), which exhibits high alkali-tolerance (Kazunobu et. al. "Remarkable alkaline stability of an engineered protein A as immunoglobulin affinity ligand: C domain having only one amino acid substitution", Protein Sci. 2013 September; 22(9): 1230-1238), was also included for comparison purpose. For each ligand, a construct with 2 SPA domains or 5 SPA domains was made. A poly-His tag and a single Cysteine residue were also added to the C-terminal end of each polypeptide. The synthesized genes were cloned into a pET21a or pET28b vector. The two domain or five-domain proteins were used as the affinity ligands for testing human IgG-binding activity. The expression cassettes were sequenced to confirm the amino acid sequence of the inserted genes. The amino acid sequences for some of the synthesized genes are listed in Table 2.

TABLE 2

Ig-binding affinity ligands

| | Mutations | SEQ ID NO: |
|---|---|---|
| 1 | Z domain (without mutations) | 14 |
| 2 | G29A (C domain with G29A mutation) | 15 |
| 3 | S41A (Z domain) | 16 |
| 4 | S41V (Z domain) | 17 |
| 5 | N52L (Z domain) | 18 |
| 6 | N52V (Z domain) | 19 |
| 7 | S41A, N52V (Z domain) | 20 |
| 8 | S41V, N52V (Z domain) | 21 |
| 9 | S41A, V52L (Z domain) | 22 |

Example 3. Protein Expression for the Ig-Binding Proteins

The pET21a and pET28b constructs bearing the genes of the Ig-binding proteins were introduced into *E. coli* BL21 cells. Briefly, about 10 ng of the purified pET28b plasmid corresponding to each gene was mixed with 100 μL of freshly made competent BL21 cells. After incubation on ice for 20 min, the cells were heat-shocked at 42° C. for 50 seconds. Then the cells were put on ice for 30 min before they were transferred into 2 mL of LB medium at 37° C. The cells were cultured for about 2 hours and plated on LB-agar plates with Kanamycin at 50 μg/mL concentration. The LB-agar plates were incubated at 37° C. for about 16 hours.

For expression test, four colonies on each plate were picked and transferred to four culture tubes with 2 mL LB medium with Kanamycin. The cells were cultured overnight to reach confluence. Four new culture tubes with 2 mL fresh LB medium with Kinamycin were prepared and about 200 µL of the overnight culture were transferred in. The cells were grown to reach O.D.600 (optic density at 600 nm wavelength) of about 0.5. About 4 µL of 0.5 M isopropyl β-D-1-thiogalactopyranoside (IPTG) was added to each tube to reach the final concentration of 1 mM. The cells were continued to grow for another 4 hours. After IPTG induction, the cells were harvested by spinning down at 12,000 rcf (Relative Centrifugal Force) for 2 min. The pelleted cells were resuspended in 400 uL of Buffer A (20 mM Tris, pH 8.0, NaCl 0.5 M, EDTA 1 mM). The cell solution was briefly sonicated on ice to lyse the cells. The sonicated solution was centrifuged at top speed to pellet the cell debris. The supernatant was collected and saved for Ni-NTA purification. Briefly, the supernatant solution was incubated with about 40 µL of Ni-NTA agarose resin (from Qiagen, Hilden, Germany) for about 2 hours. The resin was collected and washed with Buffer A for 5 times. Finally the resin was eluted with 100 µL of Buffer B (Tris 20 mM, pH 8.0, Imidazole 0.3 M, NaCl 150 mM) for three times. The pooled elution fractions were run on 4-20% SDS-page gels. Clear bands corresponding to 12 kDa were clearly shown on the gels. For the four colonies of each construct, the one with strongest expression was chosen for the large scale expression.

For large scale expression, about 2 L of LB medium was prepared in four 1-L shaking flasks with bottom-baffles. A start-culture of 200 mL was grown overnight and transferred to the 1-L flasks evenly. All the procedures were essentially the same as the small scale test expression. However, for the Ni-NTA purification, a 20-mL pre-packed Ni-NTA column was used instead of batch resins. Briefly, the supernatant of the cell lysates was injected to the column at 2 mL/min with an AKTA (GE Healthcare Life Sciences). After it was eluted, the protein was dialyzed with a Buffer C (50 mM Citrate, pH 4.5) overnight. The dialyzed protein solution was subjected to cationic exchange chromatography with a 20 mL pre-packed CM column. The protein solution was injected to the column at 2 mL/min and was eluted with a 0-100% of Buffer D (50 mM Citrate, pH 4.5, NaCl 0.5 M). The fractions corresponding to the protein was pooled. The purity of the protein was analyzed with a SDS-page.

The results confirm that the mutations do not affect the expression efficiency of SPA domains. All Z domains with the mutations as listed in Table 2 have high expression efficiency and are suitable for industrial use.

Example 4. CD Spectrum of the Ig-Binding Proteins

Circular dichroism (CD) is an excellent method for rapidly evaluating the secondary structure and folding properties of proteins. Briefly, a-helix structure have negative bands at 222 nm and 208 nm and a positive band at 193 nm, while disordered proteins have low ellipticity above 210 nm and negative bands near 195 nm. Under certain conditions, the CD spectra of various variants of a same parent protein may reflect the structural stability of those mutations.

Figure 4:
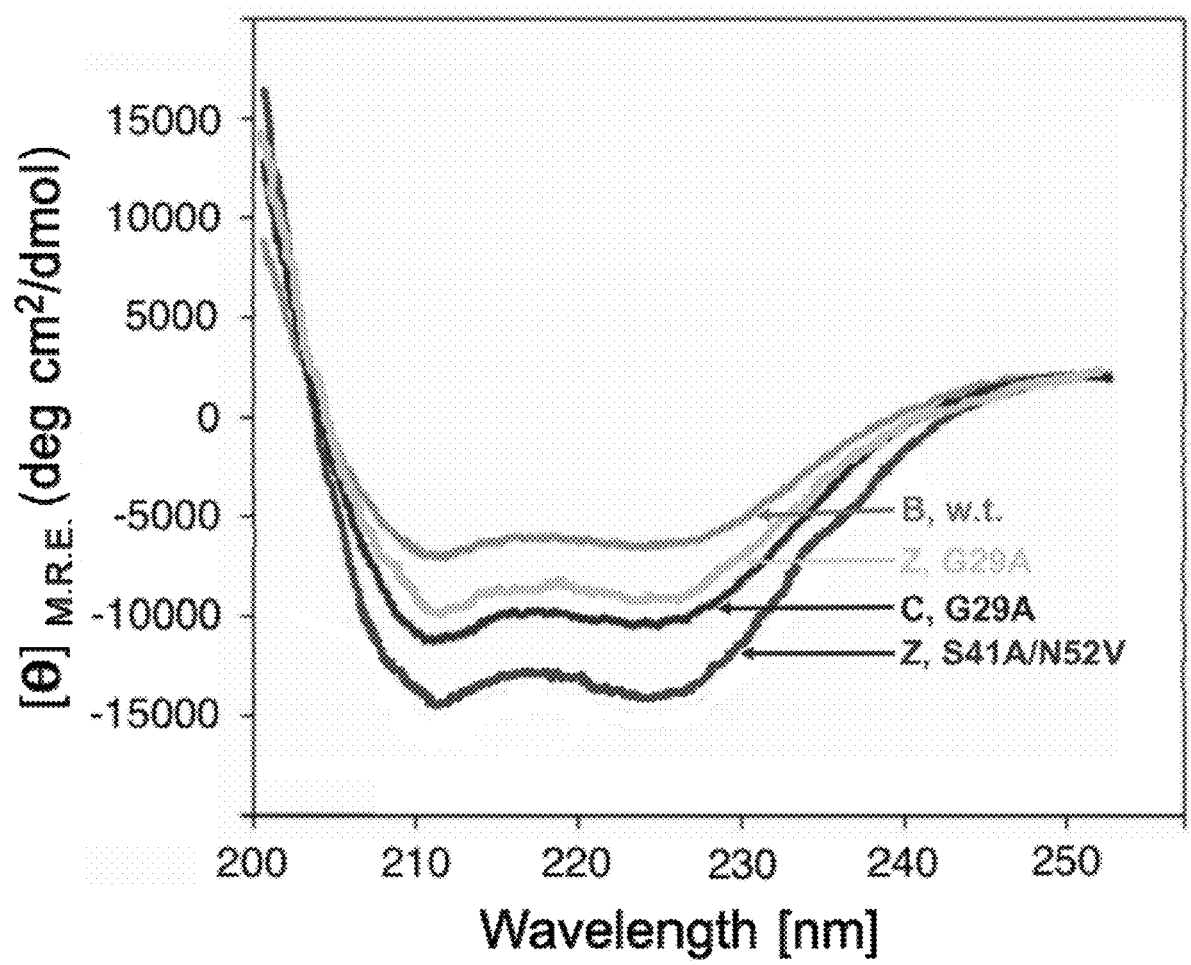
FIG. 4 shows the CD spectrum of several SPA Ig-binding domains, including domain B, Z, C (with G29A mutation) and Z (with S41A/N52V mutations) respectively at 30° C.

In this experiment, the CD spectrum of a wild type B domain polypeptide, a C domain polypeptide, a Z domain polypeptide, and a representative Z domain mutant were measured. Briefly, the purified polypeptides of the SPA domains were desalted with a P10 desalting column (GE) and the polypeptides were essentially in pure water. The protein concentration was determined by the bicinchoninic acid (BCA) assay (Pierce BCA Protein Assay Kit, Thermo Fisher Scientific). The final concentration of each protein was adjusted to 0.01 mM. CD spectra were collected on a JASCO J-710 CD spectropolarimeter in a 1 mm quartz cuvette. Data were collected between 190 and 260 nm and 10 scans at 100 nm/min and 1 s constant were taken and averaged for each spectrum. The resultant spectrums were shown in FIG. 4.

As expected, Z domain with S41A/N52V mutations had a higher percentage of α-helix structure in the solution, indicating that of a-helix structure in Z domain with S41A/N52V mutations is more stable than other Ig-binding domains.

Example 5. Coupling to an Agarose Matrix

The crosslinked agarose 4B resin was purchased from Agarose Beads Technologies (Spain). The resin serves as a basic matrix for the novel Ig-binding proteins described herein. First, the agarose beads were activated with Ethylene Glycol Diglycerol Ether. For 1.2 mL resin, about 2 mL of 0.5 M NaOH solution was added. About 0.6 mL of Ethylene Glycol Diglycerol Ether (technical grade, purchased from Sigma-Aldrich) was added. The bead solution was mixed vigorously at 23.5° C. for 18 hours. After activation, the beads were washed with deionized (DI)-water and 70% ethanol alternatively for 5 times. The beads were stored in DI-water at 4° C. before coupling.

For coupling of the ligands, the protein was first dissolved in Buffer E, which was $Na_2CO_3$ 0.1 M, pH 7.8, EDTA 5 mM, $Na_2SO_4$ 0.5 M, 2-beta-mecaptanolethanol 5 mM to reach the final concentration of 5 mg/mL. The protein solution was desalted with a desalting column containing G-50 dextran resin immediately before the coupling. For the coupling reaction, about 3.0 mL of the protein solution was mixed with the Epoxy activated agarose beads. The protein-bead solution was agitated at 30° C. for about 20 hours.

The coupled beads were harvested by washing with Buffer F (Tris 100 mM, pH 8.0, NaCl 1 M) and DI-water for at 6 times. The remaining Epoxy groups on the beads were inactivated with 3 mL of 2 M Ethaloamine, pH 9.0 for 6 hours at 30° C. The beads were further washed with at least 20 mL of DI-water before use.

Example 6. Column Packing

The ligand-coupled resins were packed into 1 mL column cartridge with an internal diameter of 0.76 cm and length of 0.25 cm. The resin slurry was first equilibrated and settled in the buffer G (Tris 20 mM, pH 7.5, NaCl 300 mM, EDTA 5 mM). The compression rate of the resin was about 1.2, wherein about 1.2 ml of settled resin slurry was packed into the 1 ml cartridge. The packed column was run at various flow rates of 0.5-2.0 ml/min with the buffer G and tested for the quality of packing with a salt-plug assay. The symmetry of the conductivity peak was confirmed and analyzed to ensure the successful packing of the columns.

Example 7. Alkali-Tolerance Test with NaOH Soaking

The packed 1-ml columns were tested for dynamic binding capacity for human IgG, before and after soaking in a 0.5 M NaOH solution. To measure the dynamic binding capacity (DBC) before NaOH soaking, a packed 1-ml column was connected on an AKTA pure chromatography system (GE Healthcare Sciences). Purified human IgG (injectable IVIG) were diluted to the concentration of 2.5 mg/ml. The void volume and the maximum of the OD280 reading of the IgG solution were determined by injecting about 1 ml of the IgG solution to the by-pass at 1.0 ml/min. The void volume was recorded as the volume that the IgG solution reached to the UV detector from the injection point. The peak of UV280 was recorded as the maximum UV absorption of the IgG solution.

The DBC of the columns were first measured before NaOH soaking. The same IgG solution was injected to each column at flow rate of 0.25 mL/min, which corresponded to 4 minutes of the residence time. The 10% breakthrough point was determined by the sharp turning of UV280 reading during column injection, wherein 10% of the maximum UV280 reading was reached. The injection was stopped at the point of the 10% breakthrough. The dynamic binding capacity (DBC) was calculated by the following equation:

$$DBC\ (mg/mL) = C_o \times (V_i - V_0)/CV,$$

wherein $C_o$ is the concentration of the antibody feedstock, $V_i$ is the total volume of the injected sample up to the 10% break point, $V_0$ is the void volume from the injection point to the detector, and CV is the column volume which is 1 ml in this case.

To determine the DBC after a NaOH soaking, the columns were manually injected with about 8 ml of 0.5 M NaOH solution with a syringe. After soaking the columns in the NaOH solution for about 24 or 35 hours, the columns were washed by injecting of plenty of 1× PBS. The columns were then tested with IgG dynamic binding capacity as described above.

The resulted DBCs for the various columns before and after 0.5 M NaOH soaking were listed in Table 3.

TABLE 3

| Column/Mutation(s) | DBC before NaOH soaking (mg/ml) | DBC after 24 h soaking (mg/ml) | DBC after 35 h soaking (mg/ml) | Percentage of remaining DBC (%) |
|---|---|---|---|---|
| S41A (Z domain) | 62 | 52 | 44 | 70.9 |
| S41V (Z domain) | 65 | 53 | 43 | 66.1 |
| N52V (Z domain) | 63 | 52 | 41 | 65.1 |
| N52L (Z domain) | 58 | 47 | 39 | 67.2 |
| S41A, N52V (Z domain) | 65 | 59 | 53 | 81.5 |
| S41V, N52V (Z domain) | 64 | 56 | 49 | 76.5 |
| S41A, V52L (Z domain) | 59 | 50 | 42 | 71.2 |
| Z domain | 61 | 43 | 30 | 49.1 |
| G29A (C domain) | 62 | 51 | 41 | 66.1 |

Figure 5:
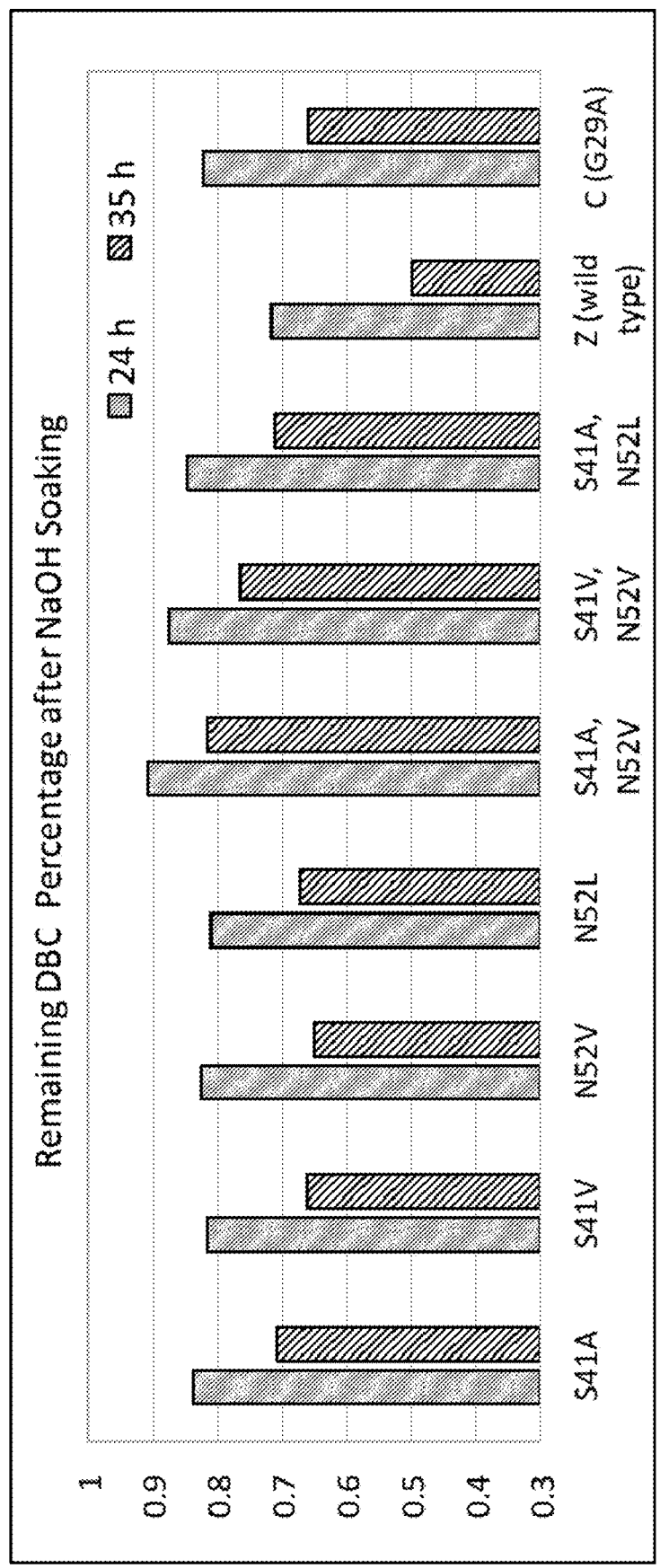
FIG. 5 shows the change of the IgG-binding capacity of various SPA IgG-binding domains with mutations including Z domain with S41A mutation, Z domain with S41V mutation, Z domain with N52V mutation, Z domain with N52L mutation, Z domain with S41A/N52V mutations, Z domain with S41V/N52V mutations, Z domain with S41A/N52L mutations, Z domain, and C domain with G29A mutation.

The summary of DBC change was also illustrated on FIG. 5. All the single mutations at R1 or R2 contributed to the increase of the alkali-tolerance of the resins. And the double mutations at R1 and R2 improved the alkali-tolerance more significantly. The IgG-binding domain variant corresponding to the double mutation S41A, N52V was selected for further DBC testing during CIP cycles in Example 7.

Example 7. DBC Change During CIP Cycles

Based on the results, the resin corresponding to the most alkali-resistant mutant (Z domain with S41AN52V mutations) was selected for CIP tests. Resins of MabSelect SuRE (GE Healthcare Sciences, Cat. GE17-5438-01) and MabSelect SuRe LX (GE Healthcare Sciences, Cat. GE17-5474-02) were the most popular affinity chromatography matrices that are currently commercially available. These resins were used for comparison purpose. Briefly, all the resins were packed into 1 mL column cartridge as described above. Purified human IgG solution with a concentration of 2.5 mg/ml was used as the binding sample. Residence time of 4 minutes was applied for the sample injection. The column equilibrating and IgG binding buffer was one AKTA A11 buffer line (1× PBS, pH 7.6). The IgG-elution buffer was on AKTA A12 buffer line (0.1 M Citrate, pH 3.0). The CIP buffer was on AKTA B1 buffer line (0.5 M NaOH). And all the columns were run on AKTA with the identical procedures and parameters. The DBC was calculated based on the method as described herein.

Figure 6:
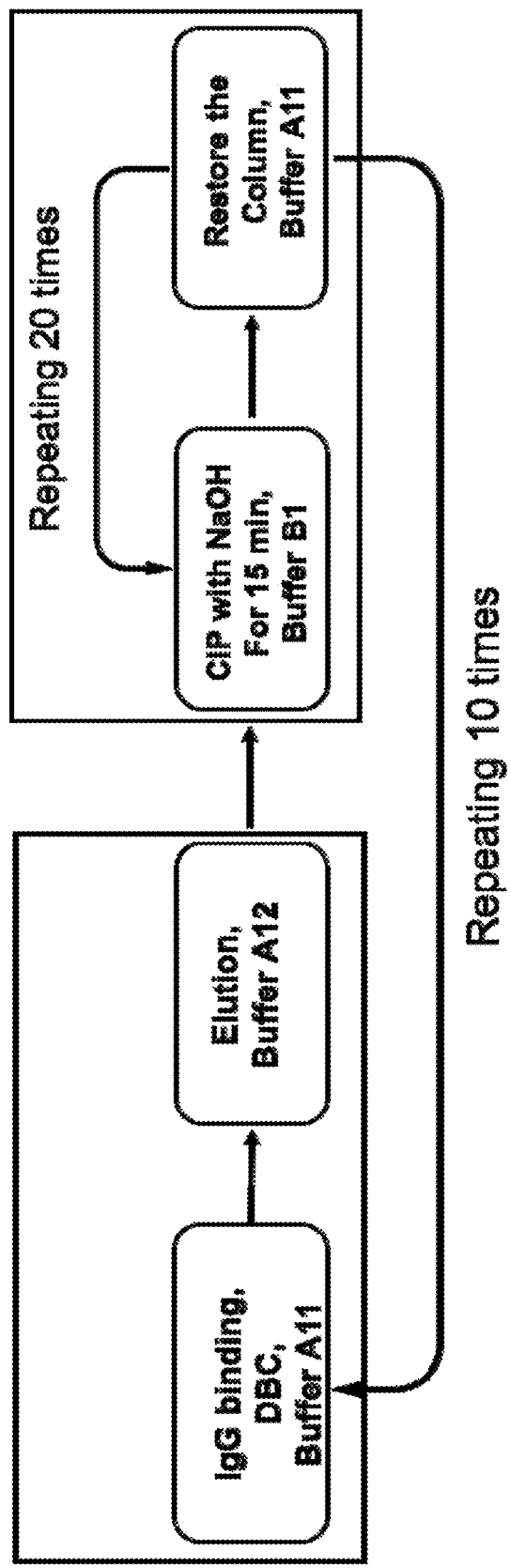
FIG. 6 shows the Clean-In-Place (CIP) testing protocol for testing alkali-tolerance.

The CIP scheme was shown in FIG. 6. Briefly, total 200 cycles of CIP with 0.5 M NaOH with 15 minutes of contact time were performed on each column and DBC measurement with the IgG solution was done every 20 cycles of CIP.

Figure 7:
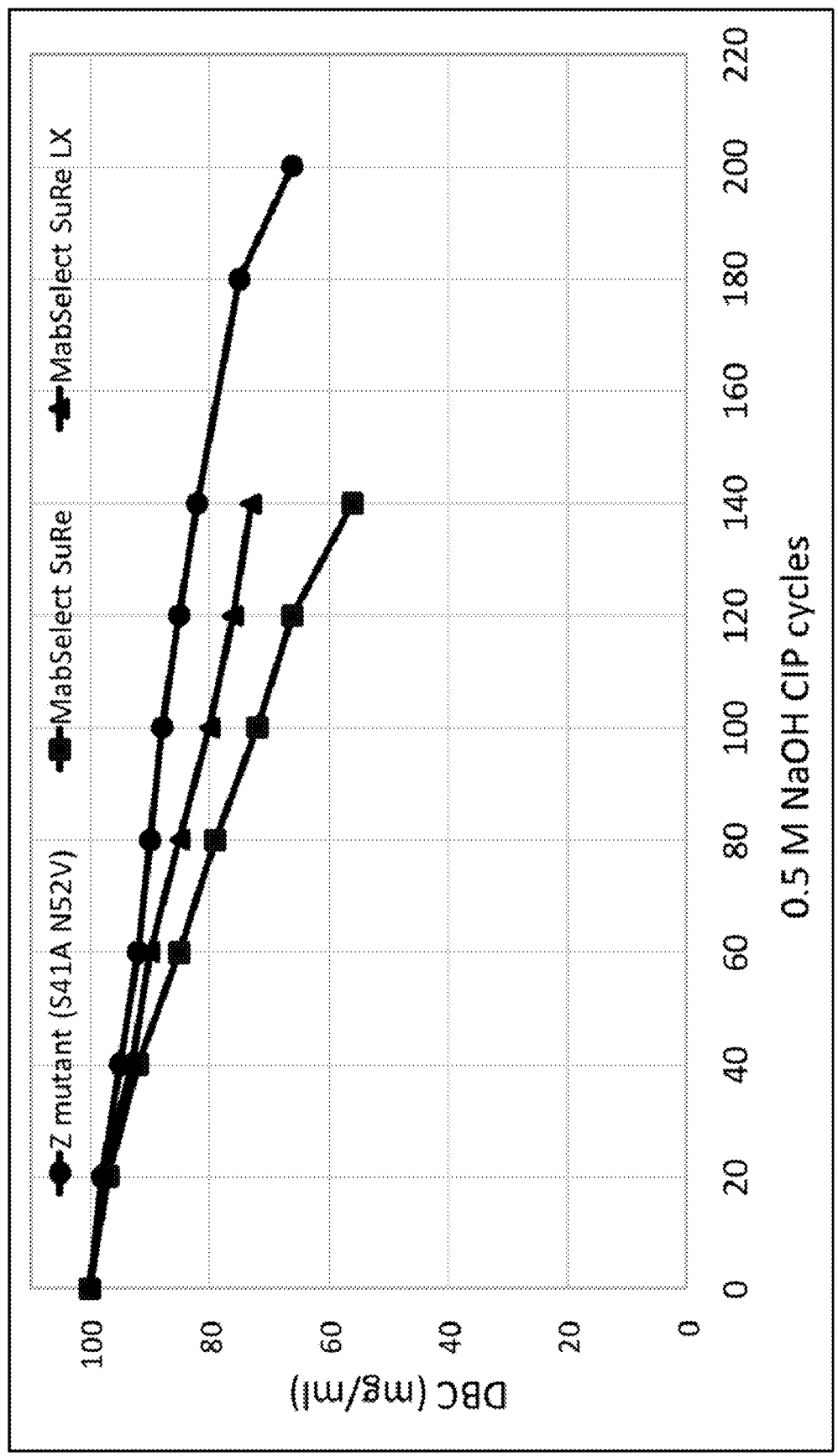
FIG. 7 shows the changing of dynamic binding capacity (DBC) of various chromatography resins after multiple cycles of 0.5 M NaOH treatment. Chromatography resins comprising Z domains with S41A/N52V mutations were compared against Mab Select SuRE and Mab Select SuRe LX, which are two commercially available resins purchased from GE Healthcare Life Sciences.

The results of DBC changing were illustrated in FIG. 7. The result shows that the resin made with the Z domain with double mutations S41A/N52V had higher alkali-tolerance than some of the popular commercial Protein A resins.

Example 8. Alkali-Tolerance Test for more Mutant Sequences

Both the B and C domain of the Protein A exhibited high alkali-tolerance. By analyzing the sequences of the all available Protein A IgG-binding domains, it indicated that the N-terminal half of the B domain and the C-terminal half of the C domain contributed significantly to the alkali-tolerance of the Protein A ligands. Therefore, several more Z and C-domain fusion variants were created with the N-terminal half of the Z domain and the C-terminal half of the C domain. All these new Protein A mutants comprised at least one mutation at S41 or N52 (the position number is based on C domain (SEQ ID NO: 5) or Z domain (SEQ ID NO: 6)). The SEQ ID NOs of the new Z/C-domain fusion variants are listed in Table 4. A multi-sequence alignment was performed between domain Z, domain C and the new Z/C domain fusion variants as illustrated in FIG. 8. Briefly, each mutated Z/C domain was connected to create a 2-repeat or 6-repeat tandem construct and cloned into the expression vector pET21b. The pET expression constructs bearing the Z/C-domain-repeats were transformed to a BL21 E. coli strain for protein expression.

The transformed E. coli strains were cultured in Lysogeny broth (LB) medium at 37° C. To induce the target protein expression, a final concentration of 0.5 mM of IPTG (Isopropyl β-D-1-thiogalactopyranoside) was added to the culture medium when the density of the E. coli cells reached to an OD600 of 0.5. Meanwhile, the temperature of the culture was adjusted to 28° C. to induce protein expression. After 16 hours of induction, the E. coli cells were harvested by centrifugation and the cell pellets were stored at −20° C. before protein purification.

The E. coli pellets containing the expressed Z/C-domain variants were thawed and dissolved in 1× PBS buffer. The bacterial solution was thoroughly sonicated at 4-10° C. to lyse the cells. The sonicated solution was centrifuged at high speed to separate the bacterial debris and supernatant. The clarified supernatants were kept for protein purification. Briefly, the supernatants were first adjusted to pH 4.6 with citric acid powder. Additional water was added to lower the conductivity of the solutions. The pH-adjusted supernatants were injected into a 5 ml CM-Sepharose cationic exchange column at a flow rate of 1 ml/min. After washing with plenty of a citrate buffer (50 mM citric acid, pH 4.6, 50 mM NaCl), the column was eluted with a high salt buffer (50 mM citric acid, pH 4.6, 600 mM NaCl). The eluted proteins were verified with SDS-PAGE electrophoresis.

The solution containing the purified proteins was adjusted to pH 8.0, with sodium carbonate. The proteins were immobilized onto epoxide-activated agarose resin and the resin was packed into the 1 ml columns as described above.

The columns were tested for dynamic binding capacity for human IgGs, before and after soaking in a 0.5 M NaOH solution. To measure the dynamic binding capacity (DBC) before NaOH soaking, a packed 1 ml column was connected on an AKTA (GE Healthcare Sciences). Purified human IgGs (injectable IVIG) were diluted to a concentration of 2.5 mg/ml. The void volume and the maximum of the OD280 reading of the IgG solution were determined by injecting about 1 ml of the IgG solution to the by-pass at a flow rate of 1.0 ml/min. The void volume was recorded as the volume that the IgG solution reached to the UV detector from the injection point. The peak of UV280 was recorded as the maximum UV absorption of the IgG solution.

The DBCs of the columns were first measured before NaOH soaking. The same IgG solution was injected to each column at a flow rate of 0.25 mL/min, which corresponded to 4 minutes of the residence time. The 10% breakthrough point was determined by the sharp turning of UV280 reading during column injection, wherein 10% of the maximum UV280 reading was reached. The injection was stopped at the point of the 10% breakthrough. The dynamic binding capacity (DBC) was determined as the following:

$$DBC\ (mg/mL) = C_o \times (V_i - V_o)/CV,$$

wherein $C_o$ is the concentration of the antibody feedstock, $V_i$ is the volume of the feedstock injected up to the 10% breakthrough point, $V_o$ is the void volume from the injection point to the detector, and CV is the column volume (1 ml in this case).

To determine the DBC after a NaOH soaking, the columns were manually injected with about 8 ml of 0.5 M NaOH solution with a syringe. After soaking the columns in the NaOH solution for about 24 hours, the columns were washed by injecting of plenty of 1× PBS. The columns were then tested with IgG dynamic binding capacity as described above.

The resulted DBCs for the various columns before and after 0.5 M NaOH soaking are listed in Table 5.

TABLE 4

Sequence of the Z/C-domain fusion mutants used for affinity ligands

| | Z/C Mutants | SEQ ID NO |
|---|---|---|
| 1 | S41A, domain 9B | 30 |
| 2 | S41L, domain 9F | 31 |
| 3 | S41A, N52V, domain 8E | 32 |
| 4 | G29K, domain 8C | 33 |

TABLE 5

DBC testing for the Z/C-domain variants

| Column/Mutation(s) | DBC Before 24 h of NaOH Soaking (mg/ml) | DBC After 24 h NaOH of Soaking (mg/ml) | Percentage of remaining DBC (%) |
|---|---|---|---|
| 6-repeat 9B | 66 | 61 | 92.4 |
| 6-repeat 9F | 65 | 55 | 84.6 |
| 6-repeat 8E | 67 | 59 | 88.2 |
| 6-repeat 8C | 69 | 55 | 79.7 |

The G29K (8C) comprising no mutations at S41 or N52 was chosen as a control sequence. The results of the DBC test after 0.5 M sodium hydroxide soaking showed that the ligands comprising one or two mutations at S41 and N52 had better alkali-tolerance than the control ligand. Among those with S41 and/or N52 mutations, the 9B (SEQ ID NO: 30) exhibited the best alkali-tolerance. Taken together with the previous tests, it indicated that the Z/C fusion domains comprising at least one mutation at S41 or N52 had equal or better alkali-tolerance.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising a first immunoglobulin (Ig)-binding domain, wherein the first Ig-binding domain comprises:
   (1) the amino acid sequence that is at least 90% identical to SEQ ID NO: 1, wherein the amino acid that corresponds to S44 of SEQ ID NO: 1 is hydrophobic;
   (2) the amino acid sequence that is at least 90% identical to SEQ ID NO: 2, wherein the amino acid that corresponds to S43 of SEQ ID NO: 2 is hydrophobic;
   (3) the amino acid sequence that is at least 90% identical to SEQ ID NO: 3, wherein the amino acid that corresponds to S41 of SEQ ID NO: 3 is hydrophobic;
   (4) the amino acid sequence that is at least 90% identical to SEQ ID NO: 4, wherein the amino acid that corresponds to S41 of SEQ ID NO: 4 is hydrophobic;
   (5) the amino acid sequence that is at least 90% identical to SEQ ID NO: 5, wherein the amino acid that corresponds to S41 of SEQ ID NO: 5 is hydrophobic; or
   (6) the amino acid sequence that is at least 90% identical to SEQ ID NO: 6, wherein the amino acid that corresponds to S41 of SEQ ID NO: 6 is hydrophobic.

2. The polypeptide of claim 1, wherein the amino acid that corresponds to N55 of SEQ ID NO: 1, N54 of SEQ ID NO: 2, N52 of SEQ ID NO: 3, N52 of SEQ ID NO: 4, N52 of SEQ ID NO: 5 or N52 of SEQ ID NO: 6 is hydrophobic.

3. The polypeptide of claim 1, wherein the first Ig-binding domain comprises one of the following amino acid sequences:
   (1) the amino acid sequence that is identical to SEQ ID NO: 1, except that both of the amino acids at position 44 and position 55 of SEQ ID NO: 1 are hydrophobic;
   (2) the amino acid sequence that is identical to SEQ ID NO: 2, except that both of the amino acids at position 43 and position 54 of SEQ ID NO: 2 are hydrophobic;
   (3) the amino acid sequence that is identical to SEQ ID NO: 3, except that both of the amino acids at position 41 and position 52 of SEQ ID NO: 3 are hydrophobic;
   (4) the amino acid sequence that is identical to SEQ ID NO: 4, except that both of the amino acids at position 41 and position 52 of SEQ ID NO: 4 are hydrophobic;
   (5) the amino acid sequence that is identical to SEQ ID NO: 5, except that both of the amino acids at position 41 and position 52 of SEQ ID NO: 5 are hydrophobic; and
   (6) the amino acid sequence that is identical to SEQ ID NO: 6, except that both of the amino acids at position 41 and position 52 of SEQ ID NO: 6 are hydrophobic.

4. The polypeptide of claim 1, wherein the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 is Ala, Val, Ile, Leu, Met, Phe, Try, or Trp.

5. The polypeptide of claim 1, wherein the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 is Ala or Val.

6. The polypeptide of claim 1, wherein the amino acid that corresponds to N55 of SEQ ID NO: 1, N54 of SEQ ID NO: 2, N52 of SEQ ID NO: 3, N52 of SEQ ID NO: 4, N52 of SEQ ID NO: 5 or N52 of SEQ ID NO: 6 is Ala or Val.

7. The polypeptide of claim 1, wherein the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 is Ala and the amino acid that corresponds to N55 of SEQ ID NO: 1, N54 of SEQ ID NO: 2, N52 of SEQ ID NO: 3, N52 of SEQ ID NO: 4, N52 of SEQ ID NO: 5 or N52 of SEQ ID NO: 6 is Val.

8. The polypeptide of claim 1, wherein the amino acid sequence comprises a sequence that is at least 90% identical to the sequence of SEQ ID NO: 11, 30, or 32.

9. The polypeptide of claim 1, wherein the polypeptide further comprises a second Ig-binding domain,
wherein the second Ig-binding domain comprises
(1) the amino acid sequence that is at least 90% identical to SEQ ID NO: 1, wherein the amino acid that corresponds to S44 of SEQ ID NO: 1 is hydrophobic;
(2) the amino acid sequence that is at least 90% identical to SEQ ID NO: 2, wherein the amino acid that corresponds to S43 of SEQ ID NO: 2 is hydrophobic;
(3) the amino acid sequence that is at least 90% identical to SEQ ID NO: 3, wherein the amino acid that corresponds to S41 of SEQ ID NO: 3 is hydrophobic;
(4) the amino acid sequence that is at least 90% identical to SEQ ID NO: 4, wherein the amino acid that corresponds to S41 of SEQ ID NO: 4 is hydrophobic;
(5) the amino acid sequence that is at least 90% identical to SEQ ID NO: 5, wherein the amino acid that corresponds to S41 of SEQ ID NO: 5 is hydrophobic; or
(6) the amino acid sequence that is at least 90% identical to SEQ ID NO: 6, wherein the amino acid that corresponds to S41 of SEQ ID NO: 6 is hydrophobic.

10. The polypeptide of claim 9, wherein the sequence of the first Ig-binding domain and the second Ig-binding domain are identical.

11. The polypeptide of claim 9, wherein the sequence of the first Ig-binding domain and the second Ig-binding domain are different.

12. The polypeptide of claim 9, wherein the first Ig-binding domain and the second Ig-binding domain are separated by a spacer domain.

13. The polypeptide of claim 1, wherein the polypeptide further comprises a second Ig-binding domain, a third Ig-binding domain, a fourth Ig-binding domain, and a fifth Ig-binding domain,
wherein each Ig-binding domain comprises an amino acid sequence that is at least 90% identical to SEQ ID NO: 6, and both of the amino acids that correspond to S41 and N52 of SEQ ID NO: 6 in each Ig-binding domain are hydrophobic.

14. A vector comprising a polynucleotide encoding the polypeptide of claim 1.

15. A chromatography ligand comprising the polypeptide of claim 1.

16. A polypeptide comprising an immunoglobulin (Ig)-binding domain, wherein the Ig-binding domain comprises:
(1) the amino acid sequence that is at least 90% identical to SEQ ID NO: 1, wherein the amino acid that corresponds to N55 of SEQ ID NO: 1 is Val;
(2) the amino acid sequence that is at least 90% identical to SEQ ID NO: 2, wherein the amino acid that corresponds to N54 of SEQ ID NO: 2 is Val;
(3) the amino acid sequence that is at least 90% identical to SEQ ID NO: 3, wherein the amino acid that corresponds to N52 of SEQ ID NO: 3 is Val;
(4) the amino acid sequence that is at least 90% identical to SEQ ID NO: 4, wherein the amino acid that corresponds to N52 of SEQ ID NO: 4 is Val;
(5) the amino acid sequence that is at least 90% identical to SEQ ID NO: 5, wherein the amino acid that corresponds to N52 of SEQ ID NO: 5 is Val; or
(6) the amino acid sequence that is at least 90% identical to SEQ ID NO: 6, wherein the amino acid that corresponds to N52 of SEQ ID NO: 6 is Val,
wherein the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 is hydrophobic.

17. The polypeptide of claim 16, wherein the amino acid that corresponds to S44 of SEQ ID NO: 1, S43 of SEQ ID NO: 2, S41 of SEQ ID NO: 3, S41 of SEQ ID NO: 4, S41 of SEQ ID NO: 5 or S41 of SEQ ID NO: 6 is Ala, Val, Ile, Leu, Met, Phe, Try, or Trp.

18. A polypeptide comprising an immunoglobulin (Ig)-binding domain, wherein the Ig-binding domain comprises SEQ ID NO: 6 with a mutation at S41, wherein S41 is substituted with a hydrophobic amino acid residue.

19. The polypeptide of claim 18, wherein the Ig-binding domain further comprises a mutation at N52, wherein N52 is substituted with a hydrophobic amino acid residue.

* * * * *

UNITED STATES PATENT AND TRADEMARK OFFICE
CERTIFICATE OF CORRECTION

| | |
|---|---|
| PATENT NO. | : 11,753,450 B2 |
| APPLICATION NO. | : 16/919827 |
| DATED | : September 12, 2023 |
| INVENTOR(S) | : Yinong Zong |

It is certified that error appears in the above-identified patent and that said Letters Patent is hereby corrected as shown below:

On the Title Page

Item (57), under the ABSTRACT, please delete the following paragraph:
"The Sequence Listing associated with this application is provided in text form in lieu of a paper copy, and is hereby incorporated by reference into the specification. The name of the text file containing the Sequence Listing is Sequence Listing.txt. The text file is 36.3 KB, and was created on Sep. 30, 2020."

And replace with:
--This disclosure relates to chromatography ligands comprising one or more domains of Staphylococcal Protein A (SPA), or any functional variants thereof, as well as methods of making and using the same.--

Signed and Sealed this
Fourteenth Day of November, 2023

Katherine Kelly Vidal
*Director of the United States Patent and Trademark Office*